(12) United States Patent
Wood et al.

(10) Patent No.: US 8,816,599 B2
(45) Date of Patent: Aug. 26, 2014

(54) EXAMINATION LIGHT APPARATUS WITH TOUCH-LESS CONTROL

(75) Inventors: Robert J. Wood, Syracuse, NY (US);
Jon R. Salvati, Skaneateles, NY (US);
Michael Curry, Syracuse, NY (US);
Christopher Dickens, Rochester, NY (US); Ervin Goldfain, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 633 days.

(21) Appl. No.: 13/057,310

(22) PCT Filed: Aug. 7, 2009

(86) PCT No.: PCT/US2009/053161
§ 371 (c)(1),
(2), (4) Date: Feb. 3, 2011

(87) PCT Pub. No.: WO2010/017481
PCT Pub. Date: Feb. 11, 2010

(65) Prior Publication Data
US 2011/0175551 A1  Jul. 21, 2011

Related U.S. Application Data

(60) Provisional application No. 61/188,396, filed on Aug. 8, 2008, provisional application No. 61/087,385, filed on Aug. 8, 2008.

(51) Int. Cl.
*H05B 37/02* (2006.01)

(52) U.S. Cl.
USPC .......................................................... 315/291

(58) Field of Classification Search
USPC ................ 315/209 R, 224, 225, 291, 307, 51
See application file for complete search history.

(56) References Cited

U.S. PATENT DOCUMENTS

| 5,716,129 | A | 2/1998 | Kunen et al. |
|---|---|---|---|
| 5,764,145 | A | 6/1998 | Hansson et al. |
| 8,063,567 | B2 * | 11/2011 | Chen ............................ 315/134 |
| 2005/0001633 | A1 | 1/2005 | Okushima et al. |
| 2005/0218913 | A1 | 10/2005 | Inaba et al. |
| 2007/0086200 | A1 * | 4/2007 | Togura et al. ................. 362/459 |

FOREIGN PATENT DOCUMENTS

| EP | 1710495 A1 | 10/2006 |
|---|---|---|
| JP | 3277313 A | 12/1991 |

OTHER PUBLICATIONS

International Search Report/Written Opinion for PCT/US2009/053161; 9 pages, Mar. 18, 2010.

* cited by examiner

*Primary Examiner* — Jimmy Vu
(74) *Attorney, Agent, or Firm* — Hiscock & Barclay, LLP

(57) ABSTRACT

An examination light apparatus including a touch-less control component that enables a user to control the apparatus without requiring physical contact between the user and the apparatus. The apparatus employs an LED control component that is configured to adapt its electrical interface to a variable quantity of light emitting diodes in order to interface with each of a plurality of lamp heads that each can include a unique arrangement and quantity of light emitting diodes. The light emitting diodes (LEDs) provide a high level of light quality, quantity and intensity (luminosity) while requiring low power consumption and low space and weight requirements and are employed without requiring a cooling fan. Uniform mechanical and electrical interfaces between the control component and other portions of the examination lamp provide for efficient and simple manufacturing of various examination light configurations.

15 Claims, 18 Drawing Sheets

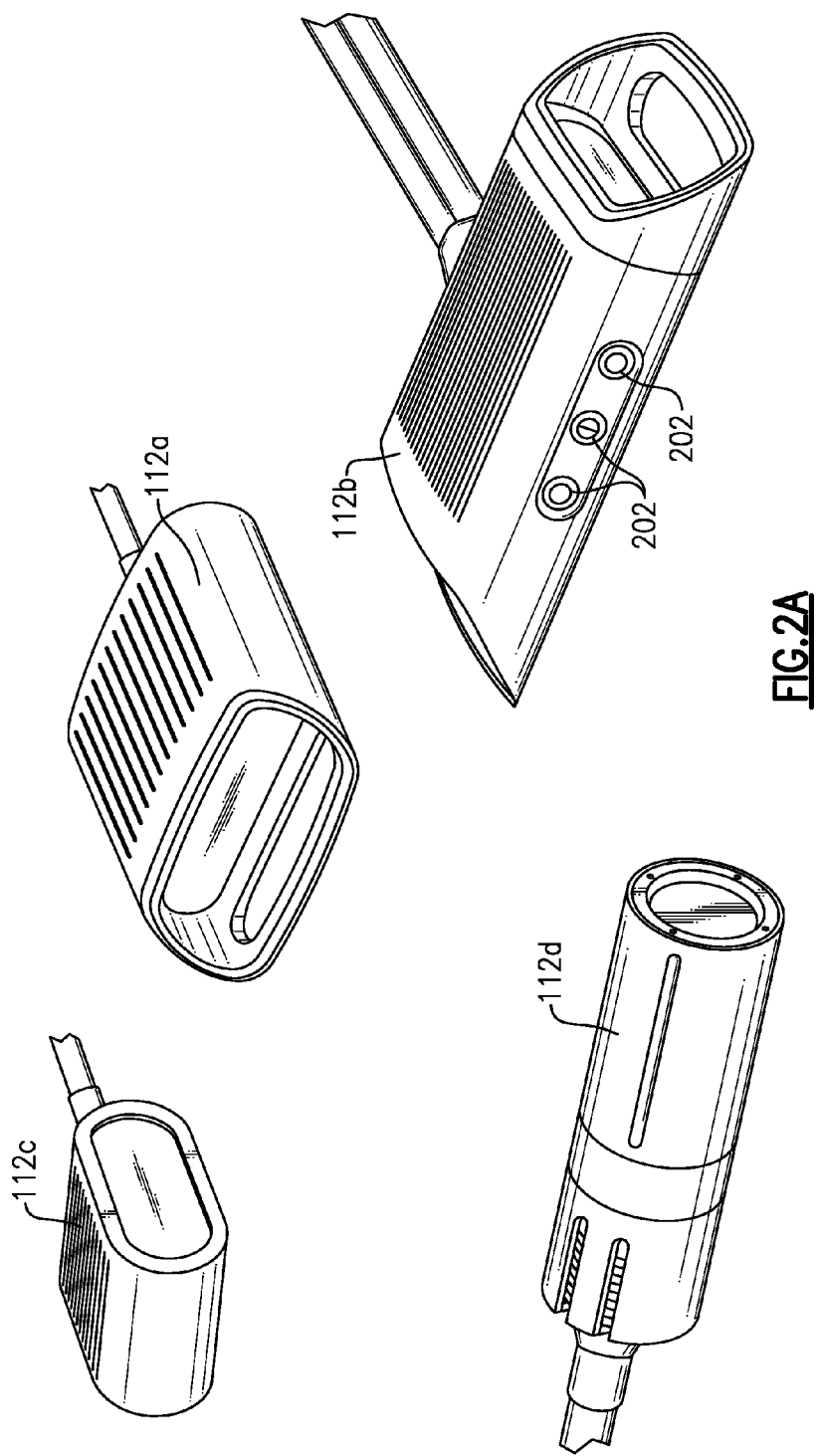

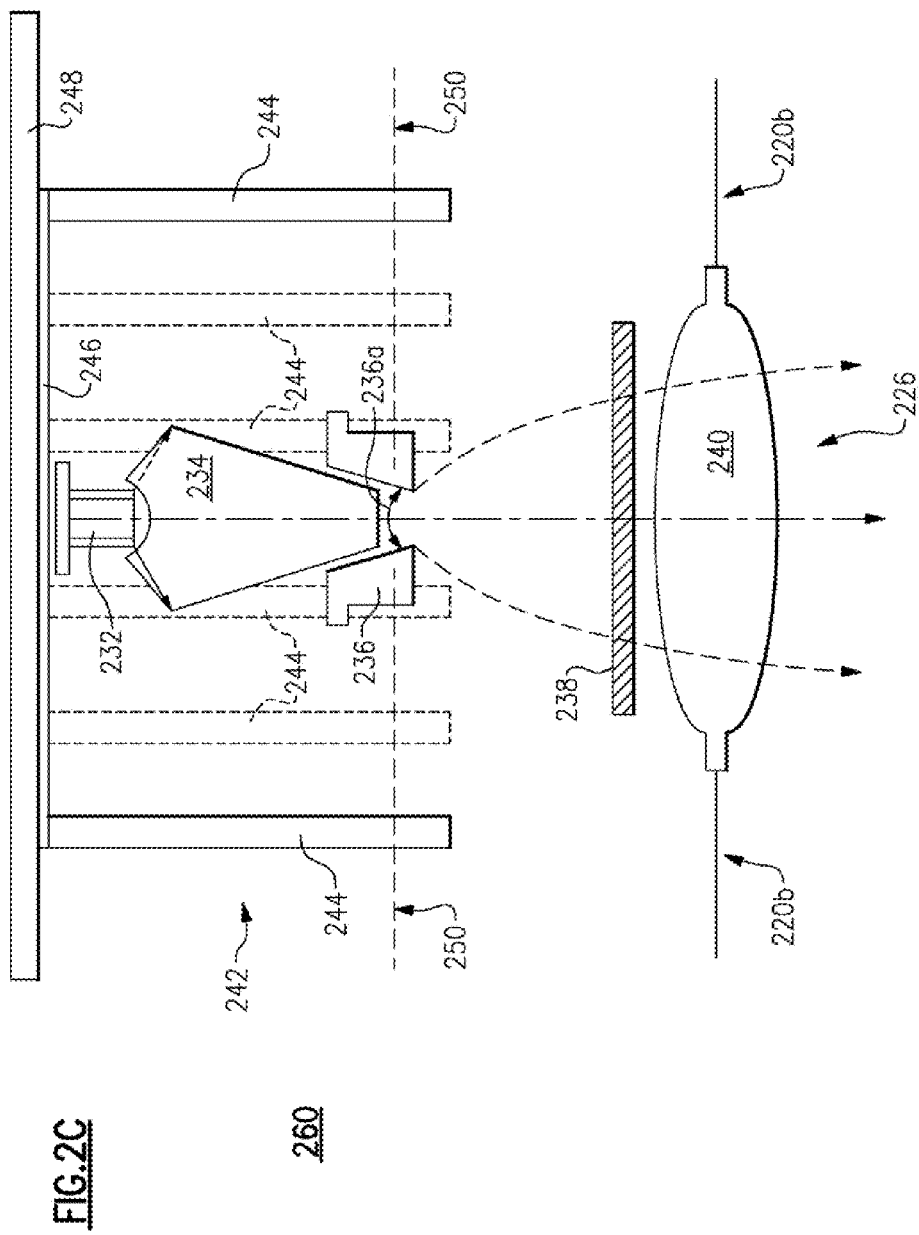

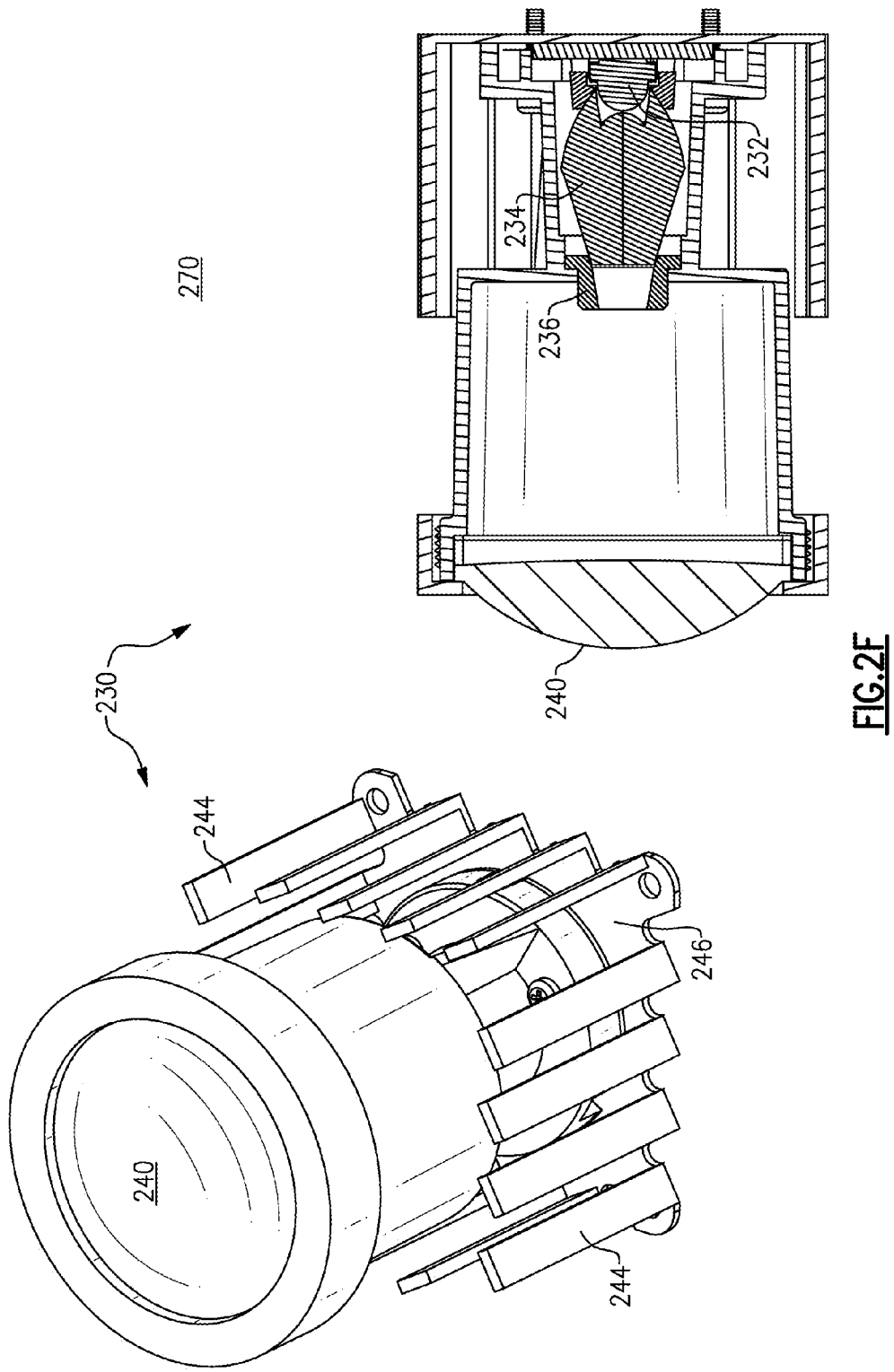

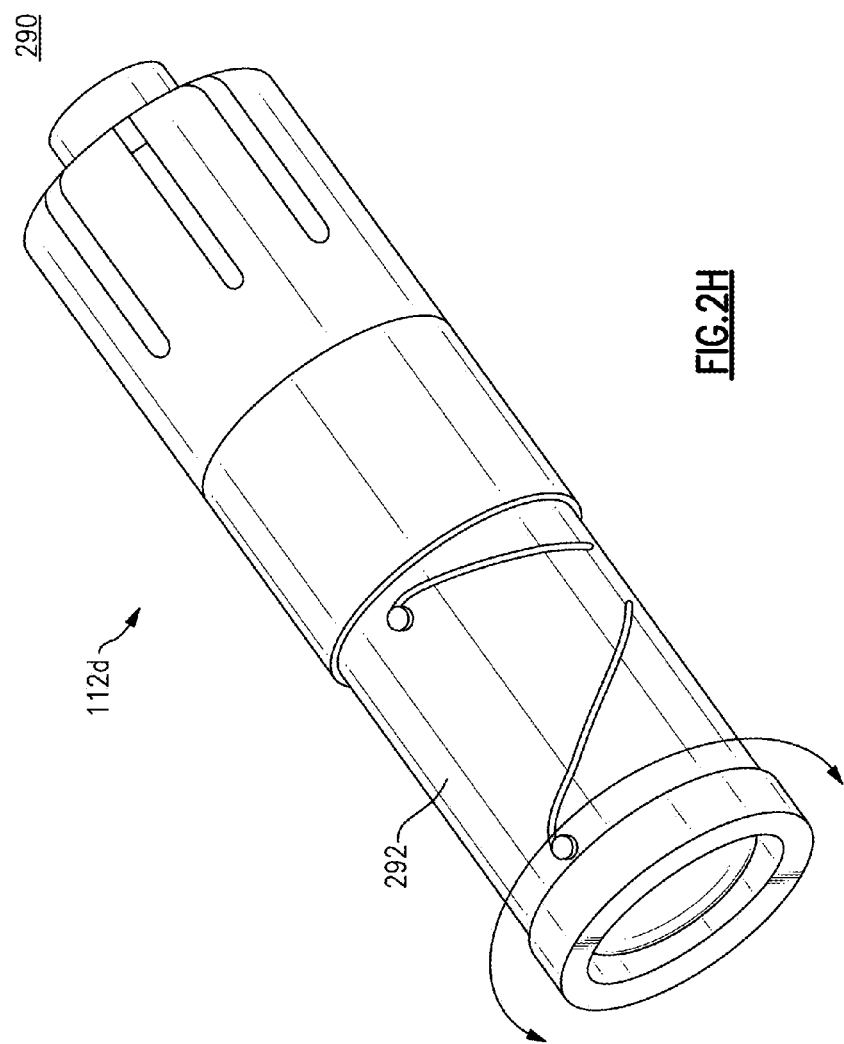

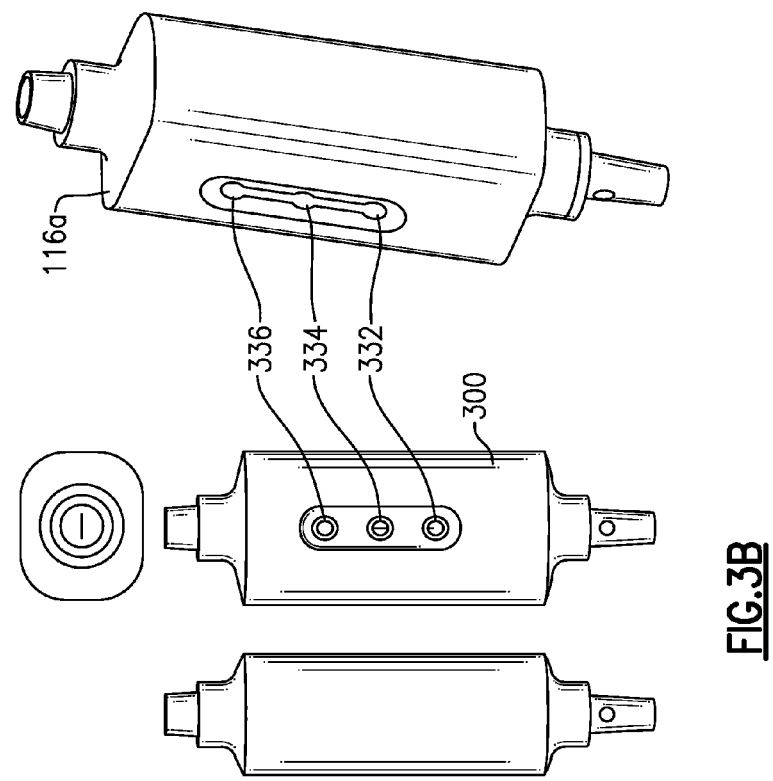
FIG.3B
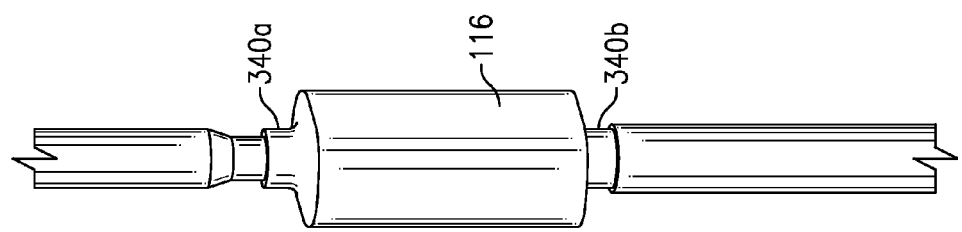

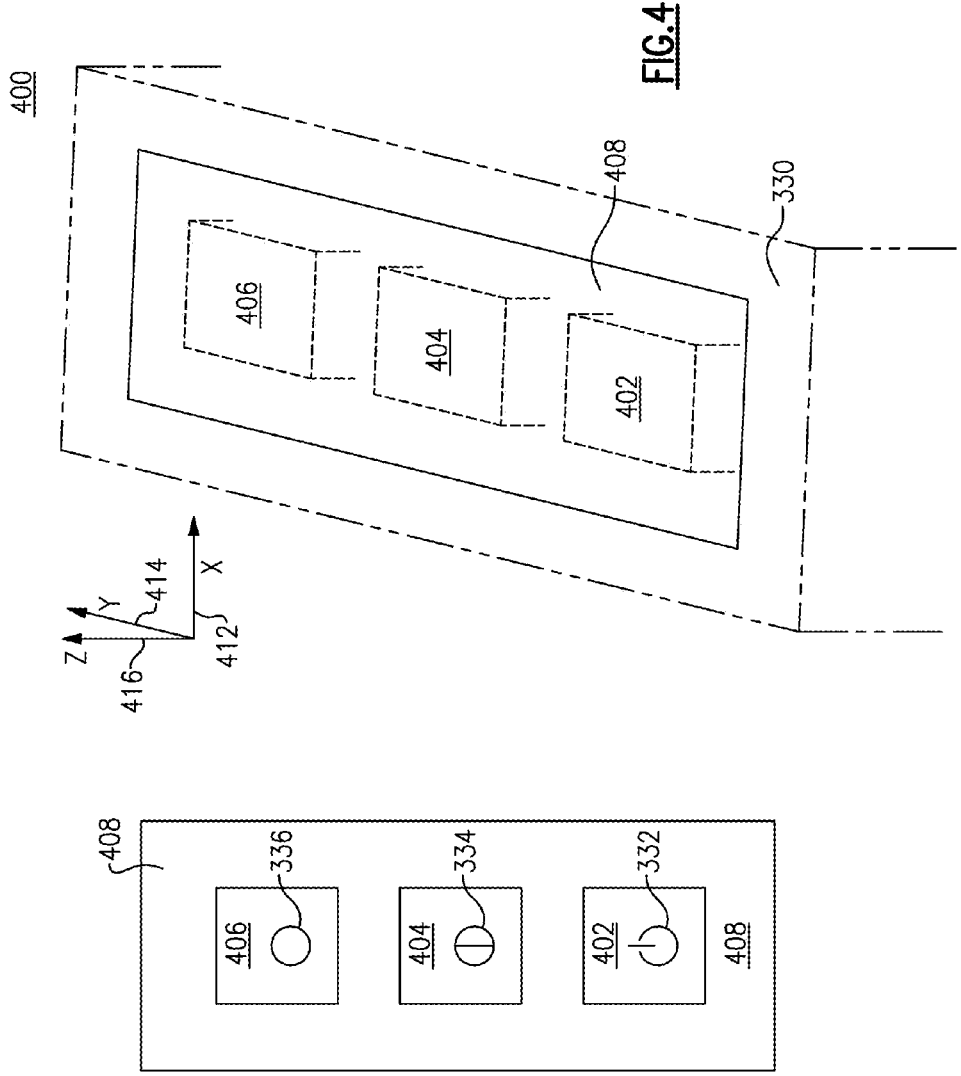

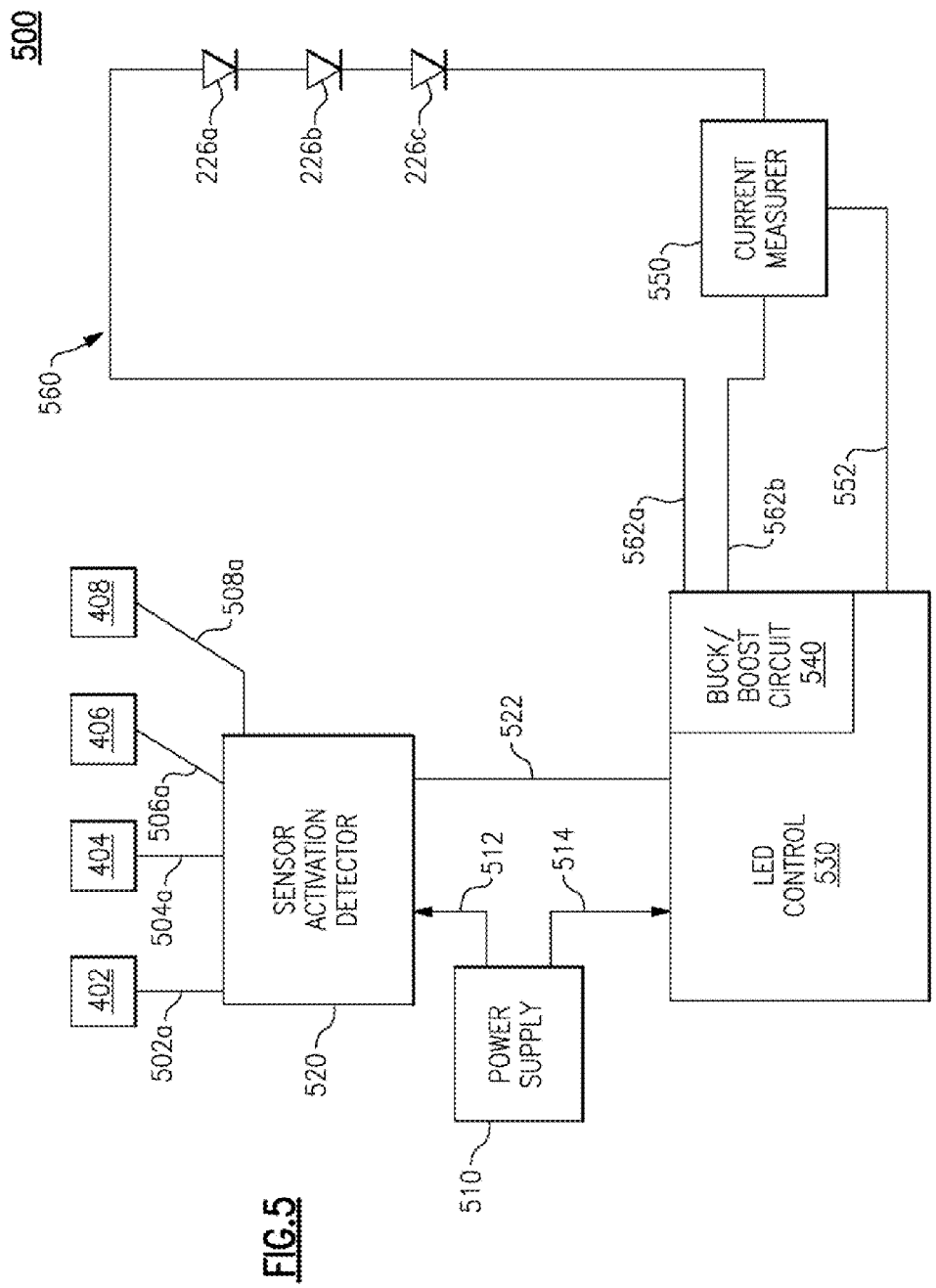

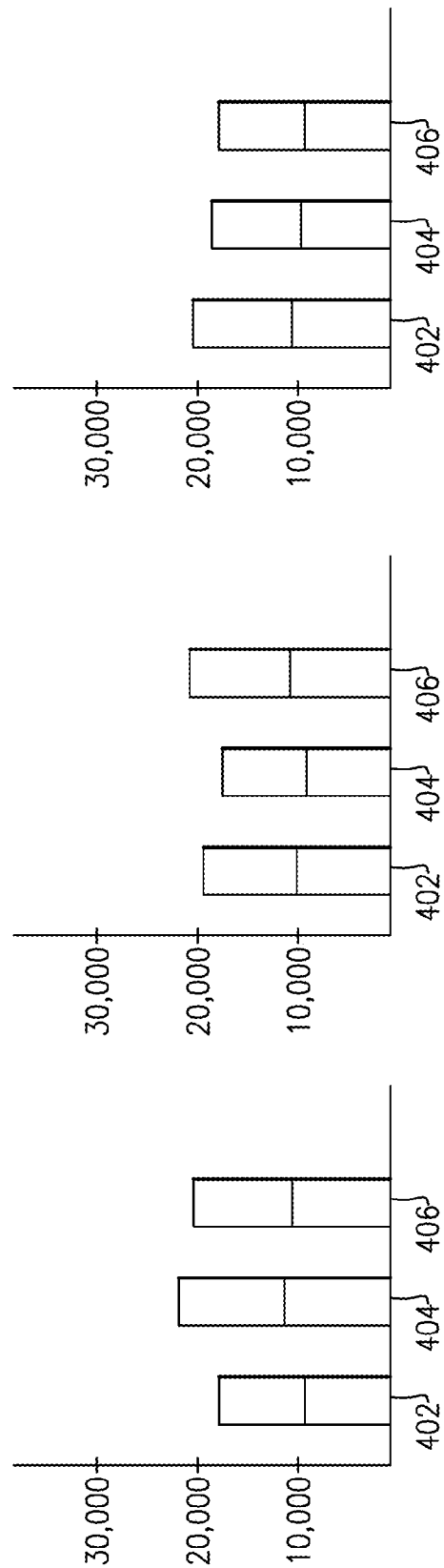

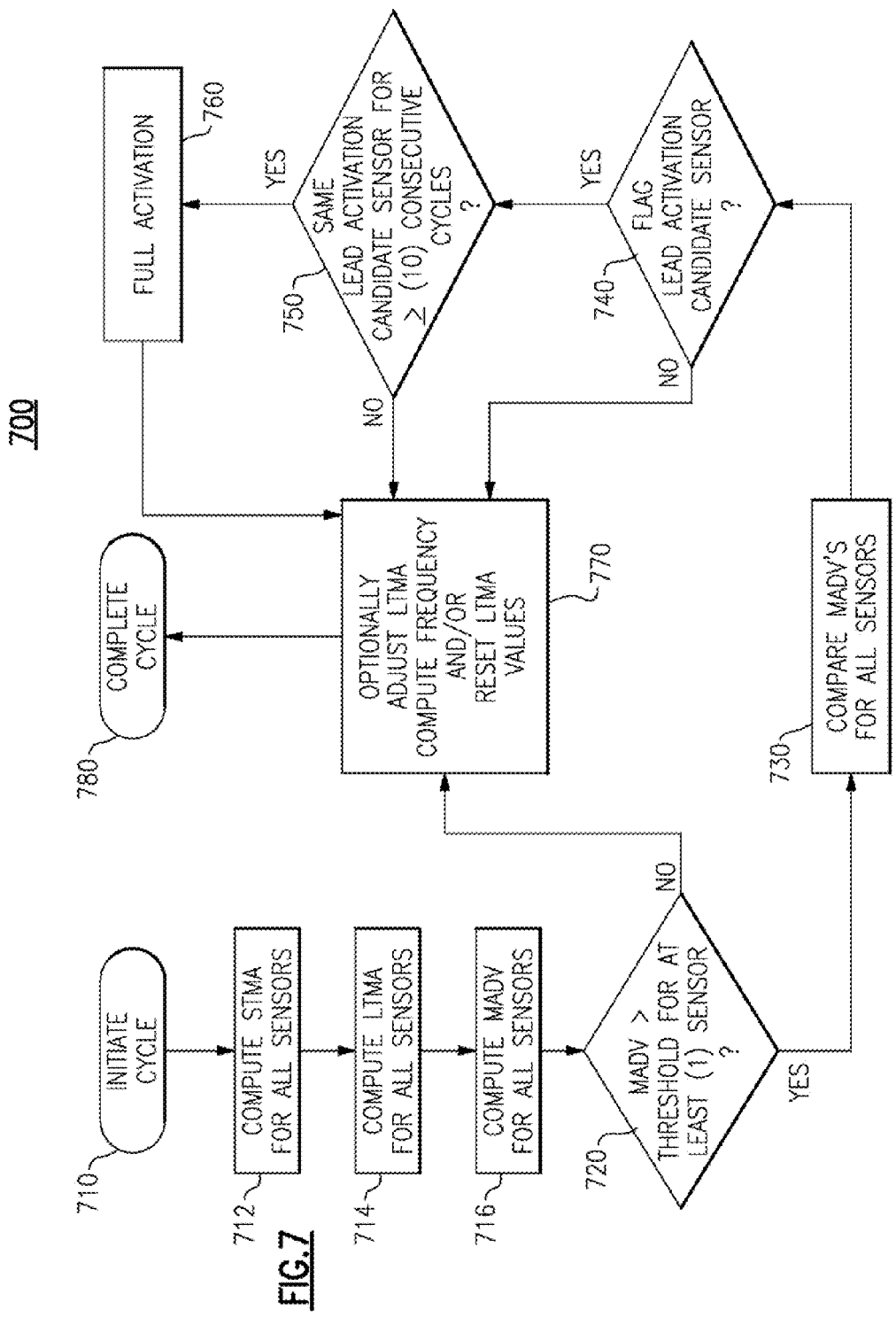

EXAMINATION LIGHT APPARATUS WITH TOUCH-LESS CONTROL

CROSS-REFERENCE TO RELATED APPLICATIONS

This U.S. national non-provisional patent application is based upon and claims priority under 35 USC §120 and 35 USC §363 to international patent application PCT/US2009/053161, filed Aug. 7, 2009, which is based upon and claims priority and benefit to, U.S. provisional patent application Ser. No. 61/087,385 that was filed on Aug. 8, 2008 and entitled "Examination Light Apparatus with Touch-less Control", and also claims priority and benefit to U.S. provisional patent application Ser. No. 61/188,396 that was filed on Aug. 8, 2008 and also entitled "Examination Light Apparatus with Touch-less Control". All of the aforementioned patent applications are incorporated herein by reference in their entirety.

FIELD OF THE INVENTION

This invention relates generally to an examination light apparatus including a contamination evasive and touch-less control component that enables a user to control the apparatus without requiring physical contact between the user and the apparatus.

BACKGROUND OF THE INVENTION

A variety of types of examination lamps are employed to direct light towards an target of interest, such as towards a patient within a health care facility. Examination lamps are typically designed to generate light of a higher intensity (luminosity) than that of general lighting, which typically employs an incandescent light source. Historically, many examination lamps have employed halogen or xenon bulbs to generate light of higher intensity (luminosity) than that of a incandescent source.

SUMMARY OF THE INVENTION

The invention provides for an examination light apparatus that is configured to be contamination evasive, scalable and portable and especially suited for employment within a health care environment, such as an environment where close up patient examination and surgery is performed. In this environment, hands of health care personnel, whether or not gloves are being worn, typically carry various forms of biological and/or chemical contamination. The contamination evasive features of the invention include a touch-less control component that enables a user, such as a health care practitioner, to control the apparatus without requiring physical contact between the user and the apparatus. The control component is further configured to include no moving parts and to include a smooth and non-porous outer surface that forms an effective barrier between inner portions of the lamp control component and contamination that could be deposited onto the lamp control component via physical contact between a user and the lamp control component. The outer surface is designed to be easily and effectively cleaned (wiped) of deposited contamination.

The scalability features of the invention include employment of a variable number (quantity) of light emitting diodes (LEDs) that provide a high level of light quality (homogeneous uniformity), quantity and intensity (luminosity) while requiring low power consumption and compact space and weight requirements. The apparatus further includes an LED control component that provides an electrical interface to control and supply electrical power to the variable quantity of LEDs. The LED control component is configured to adapt its electrical interface to a variable quantity of light emitting diodes in order to interface with each of a plurality of lamp heads that each can include a unique arrangement and quantity of light emitting diodes. Uniform mechanical and electrical interfaces between the control component and other portions of the examination lamp provide for efficient and simple manufacturing of various examination light configurations. The foregoing as well as other objects, aspects, features, and advantages of the invention will become more apparent from the following description and from the claims.

BRIEF DESCRIPTION OF THE DRAWINGS

The objects and features of the invention can be better understood with reference to the claims and drawings described below. The drawings are not necessarily to scale; the emphasis is instead generally being placed upon illustrating the principles of the invention. Within the drawings, like reference numbers are used to indicate like parts throughout the various views. Differences between like parts may cause those like parts to be each indicated by different reference numbers. Unlike parts are indicated by different reference numbers.

FIGS. 2A-2B illustrate a perspective views of a plurality of lamp heads that are incorporated into the examination lamp apparatus.

FIGS. 2C-2H illustrate views of embodiments of an illumination module that is disposed within each of the lamp heads.

FIGS. 3A-3E illustrate views of an embodiment of a touch-less and contamination evasive control component.

FIG. 4 illustrates a perspective view of the capacitance sensors and a capacitance shield located inside of the control component.

FIG. 5 illustrates a simplified conceptual diagram of electrical circuitry residing within the contamination evasive control component.

FIGS. 6A-6C each illustrate a set of capacitance count values that are obtained in association with each of the capacitance sensors during a capacitance sampling cycle.

FIG. 7 illustrates a conceptual diagram of the operation of software that executes within the sensor activation detector.

DETAILED DESCRIPTION OF THE INVENTION

Figure 1A:
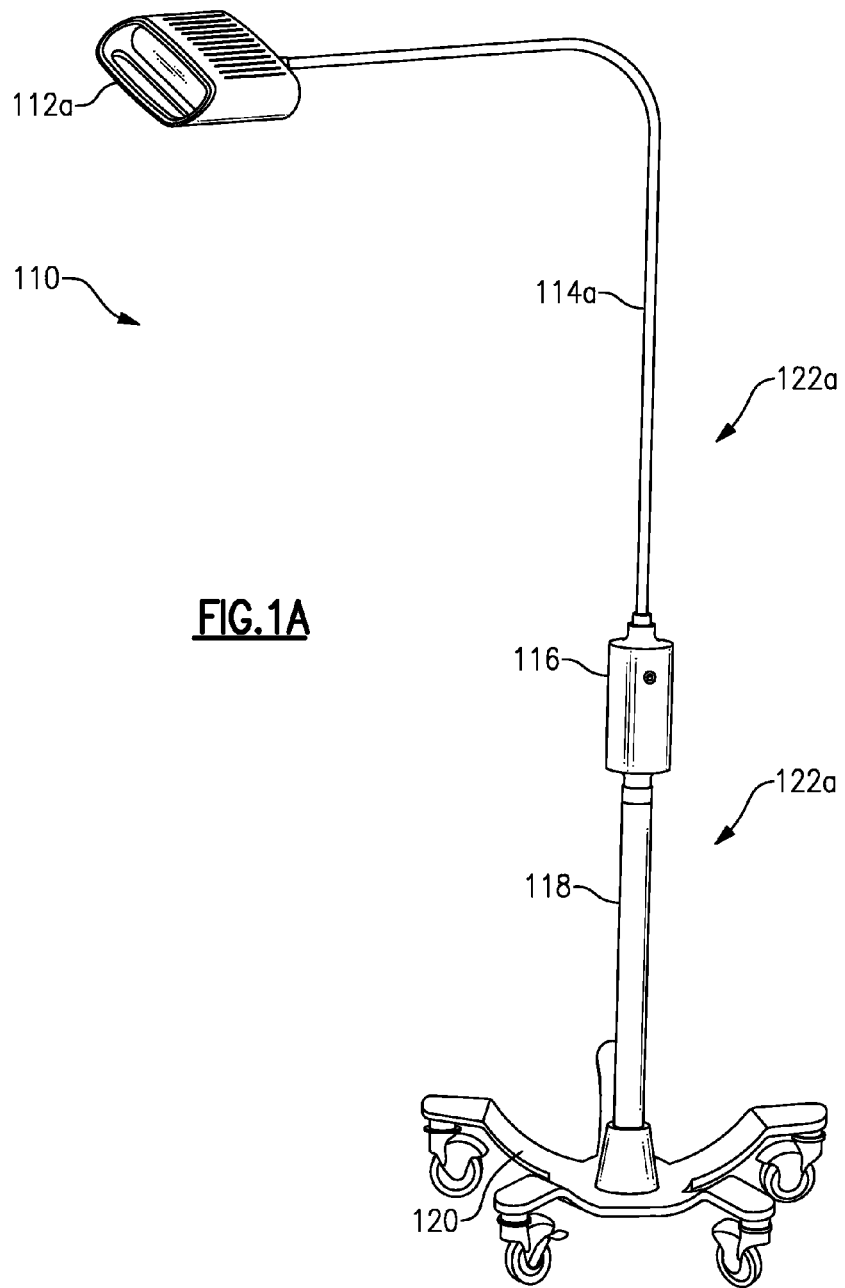
FIGS. 1A-1B illustrate two embodiments of a floor standing examination lamp apparatus.
Figure 1B:
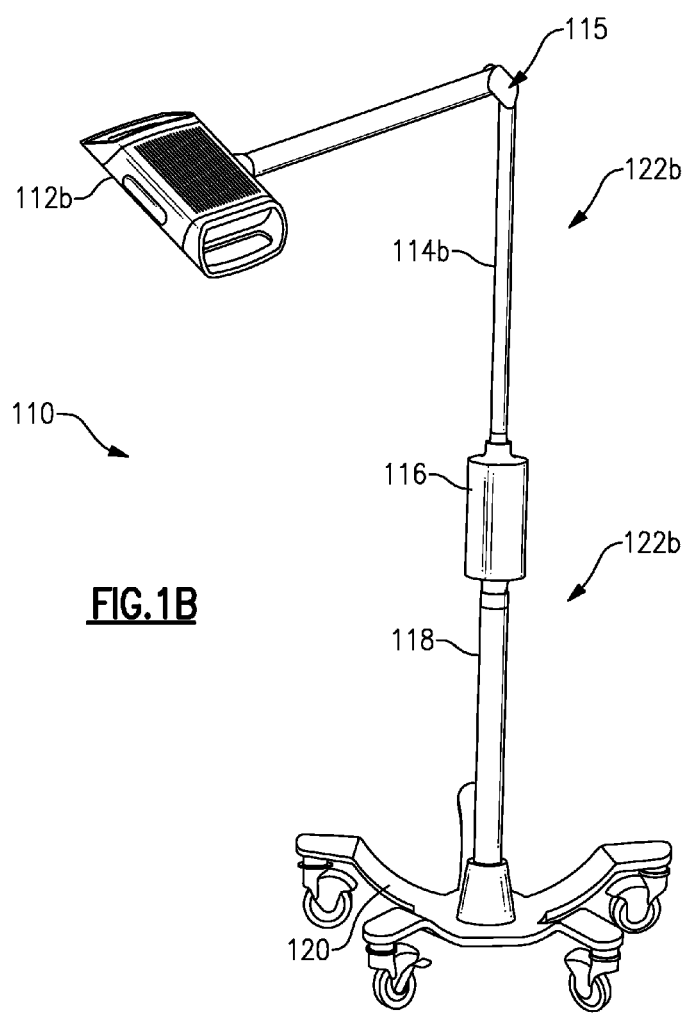

FIGS. 1A-1B illustrate two embodiments of a floor standing examination lamp apparatus. FIG. 1A illustrates an embodiment of a floor standing examination lamp apparatus 110 including a gooseneck support arm 114a. As shown, the apparatus 110 includes a lamp head 112a, an upper support 114a, a lamp control component 116, a lower support 118 and a base support 120. A body portion 122a of the assembly 110, also referred to as a lamp body 122 or body 122, is a portion of the assembly 110 that is required to physically support (secure) the position of the lamp head 112a. The base support 120 includes a plurality of wheels and is configured to enable the assembly 110 to be rolled along a floor to various locations. The assembly also includes a connection to an electrical wall outlet (not shown).

In this embodiment, the body portion 122a includes the upper support 114a, the lamp control component 116, the lower support 118 and the base support 120 of the assembly 110. Because this is a floor standing embodiment, a base support 120 is required as a portion of the body 122a to make contact with a floor surface. Other embodiments, including such as a wall mounted embodiment (not shown) of the examination lamp assembly, do not require a base support 120.

In other embodiments, the body portion 122a alternatively includes a stationary base without wheels (not shown), instead of a base 120 including wheels, as shown. In this embodiment, the control component 116 is included within the body 122a and is required to physically support (secure) the position of the lamp head 112a. In other embodiments, the control component 116, also referred to as a control box 116, is attached to but is not included within the body 122a, and is not required to physically support (secure) the position of the lamp head 112a. In these other embodiments, if the control component 116 were removed, the structure that is required to physically support (secure) the position of the lamp head 112a, namely the body 122a, would remain intact, despite the absence of the control component 116.

In the embodiment shown, the lamp head 112a includes a plurality of (3) light emitting diodes (LEDs) (See FIG. 2A) that generate light that is directed onto a target, such as a health care patient (not shown). As shown, the upper support 114a, is implemented as a gooseneck support arm 114a, also referred to as a gooseneck 114a, that is configured to enable a user to hand position and set a direction for the lamp head 112a. The lamp control component 116 provides a means for a user to control the operation of the lamp 110.

FIG. 1B illustrates a second embodiment of a floor standing examination lamp apparatus 110 including a pivot arm upper support 114b. Like the apparatus 110 of FIG. 1A, this embodiment includes a lamp head 112b, an upper support 114b, a body portion 122b, a lamp control component 116, a lower support 118 and a base support 120. The assembly also includes a connection to an electrical wall outlet (not shown). Unlike the apparatus 110 of FIG. 1B, the upper support 114b is a pivot arm type of upper support 114b that is configured to bend at a pivoting joint 115. In this embodiment, the lamp head 112b includes a plurality of (5) light emitting diodes (LEDs) (See FIG. 2C). The lamp head 112b has larger dimensions than that of the lamp head 112a and provides a different spatial arrangement of the plurality of LEDs that are disposed within it.

Figure 2B:
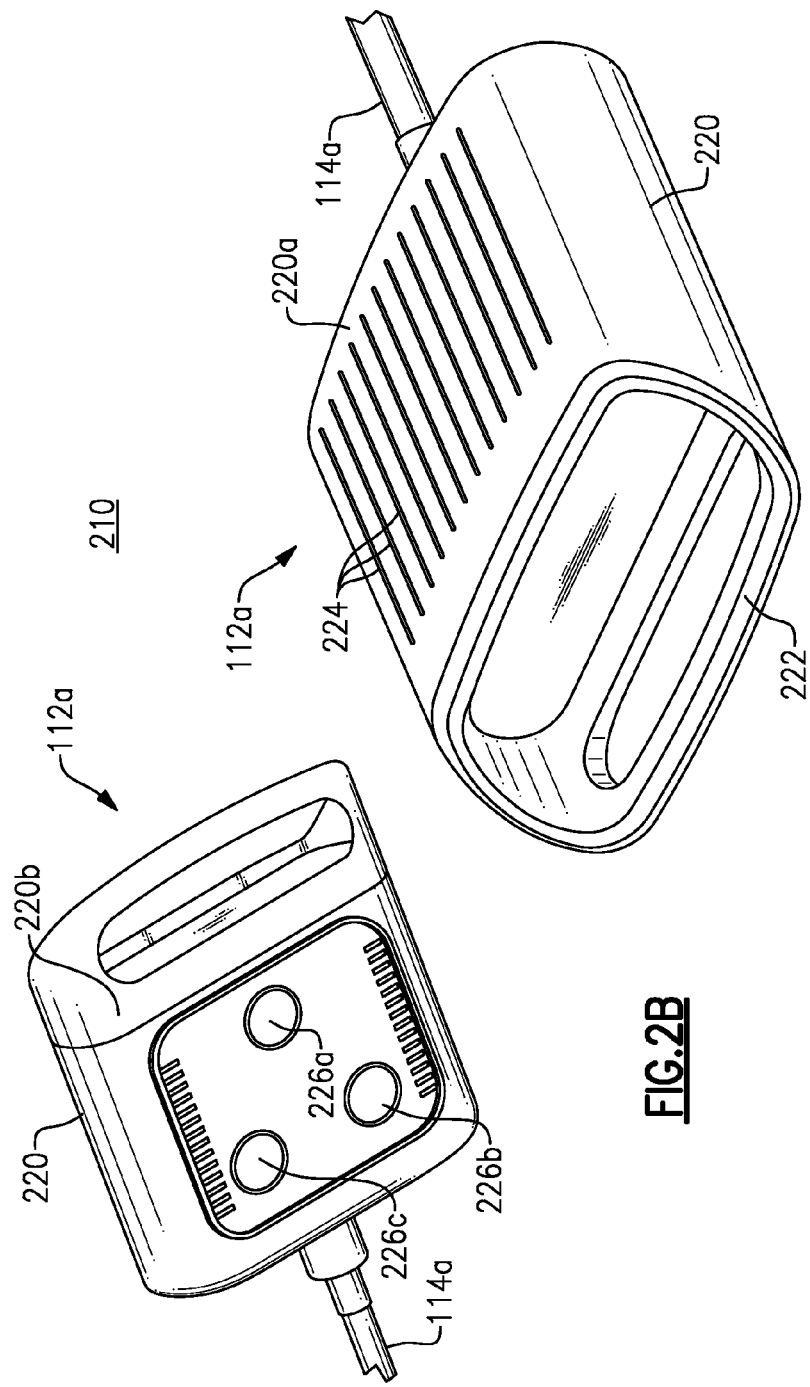

FIGS. 2A-2B illustrate at least one perspective view of each of a plurality of differently designed lamp heads 112a-112d. Each of these lamp heads 112a-112d are incorporated into at least one embodiment of the examination lamp apparatus 110. Each lamp head 112a-112d incorporates at least one light emitting diode (LED) and optical components that transform light emitted by the at least one LED into a form that is beneficial for medical use.

Referring to FIG. 2A, a perspective view 200 of each of the lamp heads 112a-112d is shown. The lamp head 112a, is incorporated into a model (LS-150) of the apparatus 110, and is shown in addition to other perspectives shown in FIGS. 1A and 2B. The lamp head 112b, is incorporated into a model (LS-200) of the apparatus 110, and is shown from a closer perspective as compared to the perspective shown in FIG. 1B. The lamp head 112c, includes one LED, and is incorporated into a model (LS-135) of the apparatus 110. The lamp head 112d, includes one LED, and is incorporated into a model (Examlight 4) of the apparatus 110.

The lamp head 112b, includes (5) LEDs and is designed to project the largest amount of light among the lamp heads 112a-112d shown here. The lamp head 112a includes (3) LEDs and is designed to project the second largest amount of light among the lamp heads 112a-112d shown here. The lamp head 112c includes (1) LED and is designed to project the third largest amount of light among the lamp heads 112a-112d shown here. The lamp head 112d includes (1) LED and is designed to project the least amount of light, among the (4) lamp heads 112a-112d shown here.

The lamp head 112d includes (1) LED and is designed to be supplied electrical power from a universal serial bus (USB) power supply. The universal serial bus (USB) power supply provides 5 watts of electrical power at 5 volts and 1 amp. The (1) LED disposed within the lamp 112d operates at 0.8 amps of current, which approximately one-half of its full operating capability of the LED, and as a result, this lamp 112d projects light at approximately one-half of the full intensity of the LED.

FIG. 2B illustrates two perspective views 210 of the lamp head 112a. The lamp head 112a is connected to the upper support 114a. In the embodiment shown, the lamp head 112a includes (3) light emitting diodes (LEDs) that are each included within an illumination module 226a-226c that are each encapsulated within a lamp head chassis 220 and that each project light out of and through a circular marked surface area 226a-226c. Reference to each illumination module 226a-226c can also refer to an LED 226a-226c disposed within each respective illumination module. Each circular marked surface area 226a-226c represents a location of a light projecting lens included within each of the illumination modules 226a-226c, each respectively including LEDs 226a-226c.

The lamp head 112a includes an outer surface (chassis) 220 that includes an upper surface 220a and a lower surface 220b and a handle 222. The upper surface 220a of the lamp head 112a includes a series of parallel heat vents 224 which function as a passageway for heat, generated by the (3) LEDS 226a-226c that are located within (internal to) the chassis 220. The heat vents 224 are configured to transfer heat away from the lamp head 112a, in order to limit the operating temperature of the lamp head 112a. The lower surface of the 220b of the lamp head 112a includes circular marked surface areas 226a-226c described above, that are disposed into a triangular arrangement 226a-226c and that each project light from each of the (3) LEDs 226a-226c that are included within the lamp head 112a.

In the embodiment shown, the lamp head 112a is electrically and mechanically connected to the upper support (gooseneck) 114a. The upper support (gooseneck) 114a includes an outer surface that is made from a non porous and smooth polymer material and an inner metallic core. The inner metallic core is configured (designed) to be bent and directed into various stationary positions via hand manipulation of the user. The outer surface is configured (designed) so that it can be easily wiped clean of contamination, via a hand held cloth, for example.

The metallic core (not shown) of the upper support 114a also includes electrical conductors (wires) (not shown) which supply electrical power to the light emitting diodes (LEDs) 226a-226c that are disposed within the light head 112. These wires are electrically connected to a circuit board that is located within the control box 116 and form a portion of a circuit that is further described in FIG. 5.

FIG. 2C illustrates a side cross-sectional view of an illumination module 230 that is disposed in quantities of one or more within each lamp head 112a-112d. The illumination module 230 includes a white LED 232 and a compact arrangement of optical components that are collectively enclosed within a heat sink 242. The illumination module 230 is shown in the context of the lamp head 112a. As shown here, the illumination module 230 includes a projection lens 240 that is disposed adjacent to the lower surface 220b of the lamp head 112a. It is the projection lens 240 of the illumination module 230 that is indicated by the circular markings 226a-226c shown in FIG. 2B.

To perform favorably within a medical (health care) environment, the illumination module 260, that is disposed inside of a lamp head 112a-112d, is designed to project a beam of light having certain desirable characteristics. In this embodiment, the illumination module is configured to project a beam of light forming a light spot, onto a surface that is substantially perpendicular to the beam of light, at a working distance of about 50 centimeters from the lamp head 112a-112d.

Within this environment, the light spot is expected to have a substantially circular (non-elongated) shape and expected to have a size with a diameter of between approximately 5-8 inches. Further, the projected light spot is to be of a uniform light intensity that is at or above a minimal acceptable light intensity and that is free of cosmetic defects such as splay lines, scratches, digs, bubbles and other similar artifacts. A projected light spot that is of uniform intensity and that is free of defects, is also referred to as being of a homogeneous quality.

As shown, a light emitting diode (LED) 232 emits a beam of light at a wide angle, approximating a 160 degree angle. The optical components 234-240 are configured to transform the beam of light that is emitted by the LED 232, prior to the beam of light being projected from the lamp head 112a-112d. Without this transformation, the beam of light that is projected from the lamp head 112a-112d could not meet the desirable characteristics that are described above.

A molded injector lens 234 is disposed at the output of the LED 232 and is configured to collect and direct the light projected from the LED 232 into a cone concentrator 236. The molded injector lens 234 has an input side that is positioned and dimensioned so that substantially all of the light emitted by the LED 232 is collected, and directed by the molded injector lens 234 into the cone concentrator 236. Without the molded injector lens 234, a substantial portion of the light that is emitted by the LED 232 would miss (not be received by) the projection lens 240.

The cone concentrator 236 is disposed at an exit face in contact with the molded injector lens 234 and is configured (designed) to collect and direct light passing through the molded injector lens 234. The cone concentrator 236 is configured to concentrate and direct light towards and through a holographic diffuser 238 and through an projection lens 240. The exit face of the molded injector lens 234 is in focus at the plane of the projected spot.

The cone concentrator 236 causes imaging not at the output (exit face) of the molded injector lens 234, but instead offsets the exit face to a location within the cone concentrator 236, that is axially separated from the exit face of the molded injector lens 234, so that light that is projected (imaged) from the illumination module is out of focus, causing cosmetic defects within the light path to be projected out of focus. Hence, the cone concentrator 236 is configured (designed) to concentrate light passing through it and configured to remove defects from the light that is passing through it.

In this embodiment, the cone concentrator 236 is manufactured by Welch-Allyn and it is made from aluminum that is shaped to form a conic tunnel having a polished reflective interior surface 236a. The light beam exiting molded injection lens 234 reflects off of the interior surface 236a.

Without the cone concentrator 236, the light beam would pass through the holographic diffuser 238b and would become overly attenuated and overspread in intensity and not be entirely received by the projection lens 240. To address this issue, the cone concentrator 236 shrinks (reduces) the beam diameter before it passes through the diffuser 238, so that the light beam exiting the diffuser 238, is not overly attenuated and overspread before received (collected by) the projection lens 240. A beam of light that is overly attenuated and overspread will not be entirely collected by the projection lens 240, and as a result, a substantial portion of the beam of light will be lost, causing the projected light spot too become too dim for desirable use.

The diffuser 238 is employed to cause cosmetic defects within the light path, such as splay lines, scratches, digs, bubbles and other artifacts to be diffused and brought out of focus to enable the projected spot to be more homogeneous and uniform in intensity. Defects within the light path are caused by the inherent structure within the surface of the LED 232 or other components 232-240 within the optical train.

Without employing a diffuser 238, the defects would remain in the beam of light that is projected by the illumination module 230 and the lamp head 112a-112d. Upon passing through the holographic diffuser 238, the light beam next passes through a projection lens 240. The projection lens 240 collects the incoming light and outputs a beam of light having dimensions that form a light spot of approximately between 5-8 inches onto a substantially perpendicular surface at a working distance of approximately 50 centimeters. As a result, a light beam of desired characteristics is projected from the illumination module 230 and the lamp head 112a-112 in an efficient manner, and more specifically in a manner with an insubstantial loss of light.

Without employing the projection lens 240, the beam of light that is projected by the illumination module would not be properly dimensioned to produce a light spot of desired size and a working distance of 50 centimeters. In some embodiments, such as with the lamp head 112d, the distance between the LED 232 and the projection lens 240 is adjustable so that the dimensions of the light beam that is projected from the illumination module 230 and the lamp head 112a-112d, is correspondingly adjustable. As shown, the projection lens 240 is disposed adjacent to the lower surface 220b of the lamp head 112a. It is the projection lens 240 that is indicated by circular markings 226a-226c shown in FIG. 2B.

The heat sink 242 has a shape of a cup having an interior (core portion) that is surrounded by a base wall 246 (inside shown) including no cooling slots and surrounded by a perimeter wall 244. The perimeter wall is structured like a fence that includes metal fins and cooling slots (air gaps) located in between the metal fins. Within the prior art, the heat sink is typically employed in such a manner where the source of heat (in this circumstance, LED 232) is disposed outside of the interior of the cup (core) portion of the heat sink 242 and adjacent to the outer side (not shown) of the base wall 246. When the source of heat is disposed outside and adjacent to the cup portion of the heat sink 242, less heat is trapped within the interior heat sink 242 and performance of the heat sink is enhanced. For reasons explained below, the prior art heat transfer enhanced configuration is contrary to how the heat sink 242 is employed within in this embodiment.

In this embodiment, the LED 232 is disposed adjacent to the inner side of the base wall 246 within the core ("cup") portion of the heat sink to reduce the space required to house the illumination module 230, and at a disadvantage of trapping more heat within the heat sink 242. Cooling slots (voids within the mounting plate 248) (Shown in FIG. 2D) are designed to counteract this disadvantage. The heat sink 242 is configured to transfer heat that is generated by the LED 232, into the lamp head 112a-112d and from the lamp head 112a-

112*d* into the atmosphere. In this embodiment, space required for the LED 232 and the heat sink 242 and the illumination module 230 is substantially reduced as compared to where the source of heat (LED 232) is disposed outside of the interior (core) portion of the heat sink 242.

In this particular embodiment, the distance between the emitting side (exit face) of the LED 232 and the cone concentrator 236 is approximately 15 millimeters, the diameter of the exiting image (exit face) of the molded injector lens 234 is about 7 millimeters, the diameter of the exiting image (exit face) of the concentrator cone 236 is about 5 millimeters and the distance between the front end (exit face) of the concentrator cone 236 and the entrance to the projecting lens 240 is about 25 millimeters. The diameter of the projecting lens 240 is about 25 millimeters. In this particular embodiment, the projecting lens is an aspherical projecting lens. In other embodiments, non-aspherical lens can be employed.

In this particular embodiment, the LED 232 employed is Luxeon LXK2-PWC4 white LED having a luminous flux of 200-220 lumens, energy consumption of approximately 6 watts, a color temperature of 5000-5650 degrees Kelvin and a forward voltage of 3.75 to 3.99 volts. The molded injector lens 234 is supplied by the Fraen SRL corporation with part number FFLI-07-LL-0. The diffuser 238 is a 5 degree holographic diffuser that is supplied by the Luminit Inc. The projection lens is a GS-1007 model lens that is supplied by the Germanow-Simon company. The heat sink is a model 500400B00000G heat sink that is supplied by the Aavid corporation. Similar components can be obtained from other manufacturers. Variations of each of the above described optical components 234-240 can be employed to yield the advantages of the invention. For example, the molded injector lens 234 can be supplied by a different manufacturer or can be configured differently to achieve the same result of collection and directing light into a concentrator cone 236.

Figure 2D:
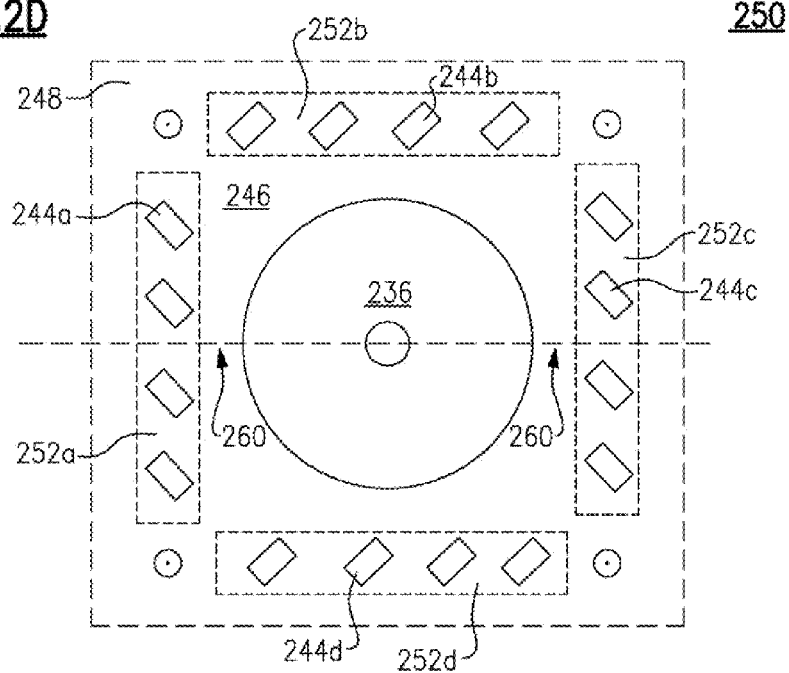

FIG. 2D illustrates an upward cross-sectional view 250 of the heat sink 242 of FIG. 2C and convection cooling slots 252*a*-252*d* (not shown in FIG. 2C). As shown, each of the sides 244*a*-244*d* of the perimeter wall of the heat sink 242 includes (4) fins that are each arranged in series along a line. Each wall is arranged as one side of a square shaped perimeter surrounding the heat sink 242. A cone concentrator 236 is disposed within the interior of the heat sink 242. From this cross-sectional view 250, a profile of the cone concentrator 236 has a circular shape. An interior side of the base wall 246 of the heat sink 242 is shown and is more distant from the viewer that the cone concentrator 236. The base wall 246 is attached to a mounting plate 248. The mounting plate 248 is more distant from the viewer than the base wall 246.

The mounting plate 248 includes (4) convection cooling slots 252*a*-252*d*. Each slot 252*a*-252*d* is implemented as a channel (void) within the mounting plate 248 which functions as a passage way for air to flow through the mounting plate 248 to cool each of the fins within each of the walls 244*a*-244*d* of the heat sink 242. Each slot 252*a*-252*d* is located and dimensioned to encompass each respective wall of fins 244*a*-244*d* of the heat sink 242, with respect to the profile shown in this view. These slots 252*a*-252*d* function to counter act the disadvantage caused by disposing and attaching the heat generating LED 232 within the interior side of the base plate 246, causing more heat to be disposed (trapped) within the interior of the heat sink 242.

The design shown results in a more compact arrangement of each illumination module 230 without requiring a cooling fan. For example, lamp head 112*b*, includes (5) LEDs that each consume about 6 watts of power. The above design allows for a compact arrangement of the (5) LEDs that collectively generate 30 watts of power, without requiring active cooling via a cooling fan. Like wise, lamp head 112*a*, includes (3) LEDs that generate (18) watts of power, without requiring active cooling via a cooling fan.

Figure 2E:
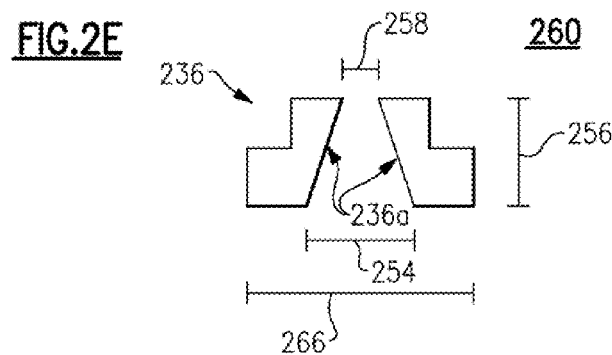

FIG. 2E illustrates a side cross-sectional view 260 of the concentrator cone 236 made of aluminum metal. As shown, the concentrator cone 236 is oriented to project light upwards to be consistent with the cross-sectional view 260 of FIG. 2D. Note that the cone concentrator 236 is shown as projecting light downwards in FIG. 2C. The cone concentrator 234 has a base diameter 256 equal to approximately 0.4 inches and a length equal to 0.187 inches. A shown, light enters the cone concentrator 236 from its bottom side and exits from its top side through a tunnel having highly polished interior surface 236*a*. An entrance 254 of the cone concentrator 236 has a diameter equal to 0.29 inches. The exit 258 of the cone concentrator has a diameter equal to 0.213 inches.

FIG. 2F illustrates a perspective view and a second side cross-sectional view 270 of the illumination module 230. From the perspective view on the left hand side of this figure, the light emitting surface of the projection lens 240 and a portion of the inside of the base wall 246 is shown. Also from this perspective view, the fins of the side wall 244 of the heat sink are angled as shown. From the second side cross-sectional view on the right hand side of this figure, the LED 232, the molded injector lens 234, the cone concentrator 236 and the projection lens 240 are arranged like shown in FIG. 2C.

Figure 2G:
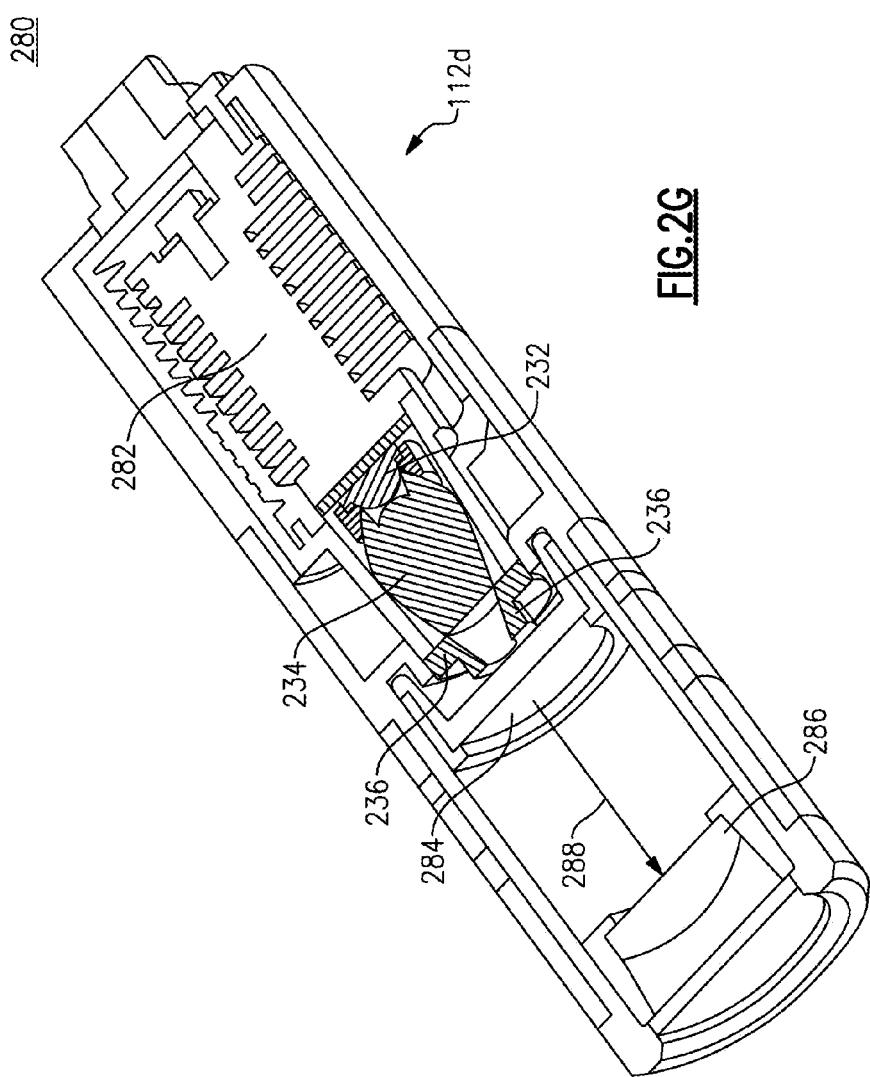

FIG. 2G illustrates a perspective cross-sectional view of an alternative embodiment 280 of the illumination module within the lamp head 112*d*. Like the first embodiment 230 of the illumination module, this alternative embodiment includes the LED 232, the injector lens 234 and the cone concentrator 236. Unlike the first embodiment 230 of the illumination module, this alternative embodiment excludes the holographic diffuser 238 and the heat sink 242 of the first embodiment 230 (shown in FIG. 2C), and instead includes an alternative heat sink 282 and a first zoom lens 284 and a second zoom lens 286.

In this alternative embodiment, a distance 288 between the first zoom lens 284 and the second zoom lens 286 is adjustable via a rotating sleeve (shown in FIG. 2H). The absence of a diffuser 238 causes the light spot that is projected from this embodiment to have a sharp edge. Defects within the light path are removed via the cone concentrator 236 in the same manner as described for the first embodiment 230 of the illumination module.

FIG. 2H illustrates a perspective view 290 of the lamp head 112*d* including the alternative embodiment 280 of the illumination module. As shown, the lamp head 116*d* includes rotating sleeve 292. Movement (rotation) of the rotating sleeve 292 causes a change to (adjusts) a distance between the first zoom lens 282 and the second zoom lens 284 of the illumination module 280 of FIG. 2G. An adjustment to the distance between the first zoom lens 282 and the second zoom lens 284 causes the dimensions of the light spot projected by the lamp head 112*d* to change.

Figure 3A:
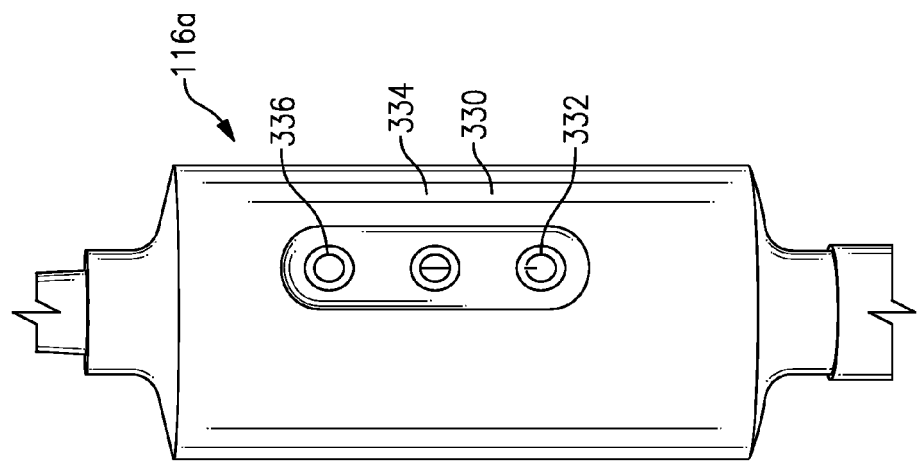
Figure 3A:
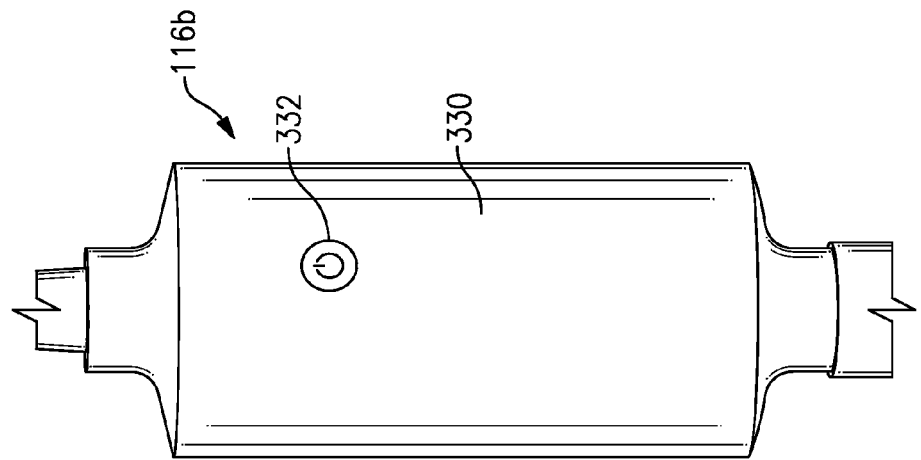

FIGS. 3A-3B illustrate a side perspective view of embodiments of a touch-less control component. FIG. 3A illustrates a side perspective view of two embodiments of a "touch less" control component 116*a* and 116*b*, which are collectively referred to using drawing reference number 116. This control components 116*a*-116*b*, also each referred to as a control box 116*a*-116*b*, each enable a user to control the operation of the apparatus 110 without requiring physical contact between the user and the apparatus 110.

In this embodiment, each of the control boxes 116*a*-116*b*, include an outer surface 330 that is configured to provide a barrier between inner (below the outer surface) portions of the control box 116, and contamination that could be deposited upon or within the control box 116a-116b, via physical contact between a user and the control box 116a-116b, whether or not the user is wearing gloves.

The outer surface 330 is preferably manufactured from a material that is free of surface pockets and that is impermeable to ingress of particulate or liquid matter, such that it forms an effective seal between the outside surface 330 and the internals of the control box 116a-116b. The term "free of surface pockets" refers to an absence of cavities that are visible to the human eye and an absence of cavities that are each dimensioned to collect a deposit of particulate or liquid contamination that would resist removal from the cavities via application of a wipe cloth, for example. In this embodiment, the outer surface 330 is made from a plastic that is referred to as "PC-ABS" which is an acronym for polycarbonate—acrylonitrile butadiene styrene. In other embodiments, the control box 116a-116b can be made from other non-porous material, that can function as an effective seal of contamination.

The outer surface 330 has a topology that is configured to have a smooth and continuous contour that excludes surface discontinuities, such as small cavities and crevasses, in order to accommodate fast and effective surface cleaning, such as surface cleaning obtained via wiping of the outer surface 330 using a hand held cloth. Small cavities (pockets), crevasses and surface discontinuities can collect and trap contamination, such as particulate or liquid contamination, that is not easily removed via wiping of the surface via a hand held cloth.

As shown, the outer surface 330 of control box 116a includes (3) markings 332-336 and the outer surface 330 of control box 116b includes (1) marking 332 that each indicate a location of an associated electrical capacitance sensor (not shown), also referred to as a capacitance sensor or sensor, that is located below the outer surface 330 and proximate to each respective sensor. Each electrical capacitance sensor functions as part of a control switch that can be activated by a user. One sensor is disposed (located) below the outer surface 330 and proximate to each of the markings 332-336. Each electrical capacitance sensor is configured (designed) to detect a source of capacitance, such as capacitance associated with an appendage (finger) of the user, when that finger is located within a range of proximity from the electrical capacitance sensor.

The result of activation of a capacitance sensor, referred to as an activation event, is effectively like a result of an action associated with pressing a button or flipping a switch. Instead of making physical contact with a button or switch, the user gestures with an appendage, such as placing a finger within proximity of a marked area 332-336 on the outer surface 330 of the control box 116. A set of electronics (not shown), including an associated sensor, that are disposed within the control box 116, are configured (designed) to detect such a gesture of the user.

Upon detection of an activation event, a predetermined action that is associated with the marking 332-336 and its hidden sensor (not shown) is performed. In some embodiments, an action that is associated with a marking 332-336 can be configured to be dynamic and be dependent upon a current state of operation of the examination light assembly.

The range of proximity for detection/activation with respect to the location of a finger of the user is configurable (adjustable) for each sensor. In some embodiments, the range of detection of a sensor is configured to require a user to position a finger to make physical contact with (touch) the marking 332-336 associated with the sensor. In other embodiments, the range of detection is configured to require a user to position a finger within a range of distance above of the marking 332-336 associated with the sensor, for a sufficient period of time. The most proximate (nearest) portion of this range is referred to herein as near proximity and the least proximate (farthest) portion of this range is referred to herein as far proximity.

In this embodiment, for example, the range of detection for a particular sensor 332-336 is where a finger is located within 0.75 inches from the outer surface 330 of the control box 116. In this embodiment, the near proximity of the range is less than 0.75 inches. To cause an activation event, the finger resides in that location for a period of time of approximately 0.5 seconds. Hence, when a user positions a finger within 0.75 inches away from a marking 332-336 for a period of time equal to 0.5 seconds or longer, an associated sensor located below that marking 332-336 and the electronics with in the control box detects the presence of that finger, and optionally activates to perform a pre-determined action. Both of the above embodiments are classified as operating in a "near field" mode of capacitance, because a portion of the user's body is required to be near (within about (2-3) inches) from a sensor so that the user can unambiguously gesture (point to) a particular sensor that is located among other sensors.

In another embodiment, the sensitivity of the sensor is raised so that the near proximity distance value of this range is within 1.0 inches relative to the outer surface 330 of the control component 116. In yet other embodiments, the sensitivity is further raised and the near proximity is within 2.0 inches, or alternatively further raised so that near proximity is within 3.0 inches. Note that activation can occur at distances farther than the near proximity distance, but there is a lower likelihood of this occurrence and there is no guarantee that it will happen in any particular circumstance. The control component 116 is designed to detect an activation event with a substantially high likelihood when a finger is positioned at less than or equal to the near proximity distance value. Positioning a finger at farther distances are less likely to cause an activation event. The likelihood of activation is an inverse function of the distance between the finger and the outer surface 330 of the control component 116.

The following describes an operational embodiment of the examination light assembly 110 for the control box 116a. In this embodiment, each of the sensors associated with the markings 332-336 of the control box 116a are configured to perform the following actions upon activation.

By default, when electrical power is first supplied to the assembly 110 by plugging its electrical connection into a wall outlet, the apparatus 110 enters an initial operating state where no light is projected. In this operating state, activation of an OFF switch represented by marking 332 performs no action, activation of a half light intensity switch 334 represented by marking 334 causes the lamp head 112 to project light at half intensity and activation of a full light intensity switch represented by marking 336 causes the lamp head 112 to project light at full intensity.

In this control box 116a embodiment, when the lamp head 112 is projecting light, activation of an OFF switch represented by marking 332 causes the lamp head 112 cease projecting light, activation of a half light intensity switch 334 represented by marking 334 causes the lamp head 112 to project light at half intensity and activation of a full light intensity switch represented by marking 336 causes the lamp head 112 to project light at full intensity.

For an embodiment including the control box 116b, which includes the (1) marking 332. This marking 332 acts as an ON/OFF switch instead of an OFF switch. By default, when electrical power is first supplied to the assembly 110 by plugging its electrical connection into a wall outlet, the apparatus 110 enters an initial operating state where no light is projected. In this operating state, activation of an ON/OFF switch represented by marking 332 causes the lamp head 112 to project light at some default intensity.

In this control box 116b embodiment, when the lamp head 112 is projecting light, activation of the ON/OFF switch represented by marking 332 causes the lamp head 112 cease projecting light. In this embodiment, the ON/OFF switch toggles between (2) states, namely projecting light and not projecting light.

FIG. 3B illustrates a side perspective views of the "touch less" control component 116. As shown, the control box 116 has an upper connection 340a and a lower connection 340b. Optionally, the lower connection attached to a wall mounted support (not shown), instead of a lower support 118 of a floor standing apparatus 110 (See FIGS. 1A-1B).

Also shown is a translucent perspective view of the control box 116a including sensors. As shown, each marking 332-336 drawn on the outer surface 300 of the control box 116 is associated with a sensor located inside of the control box 116a.

Figure 3C:
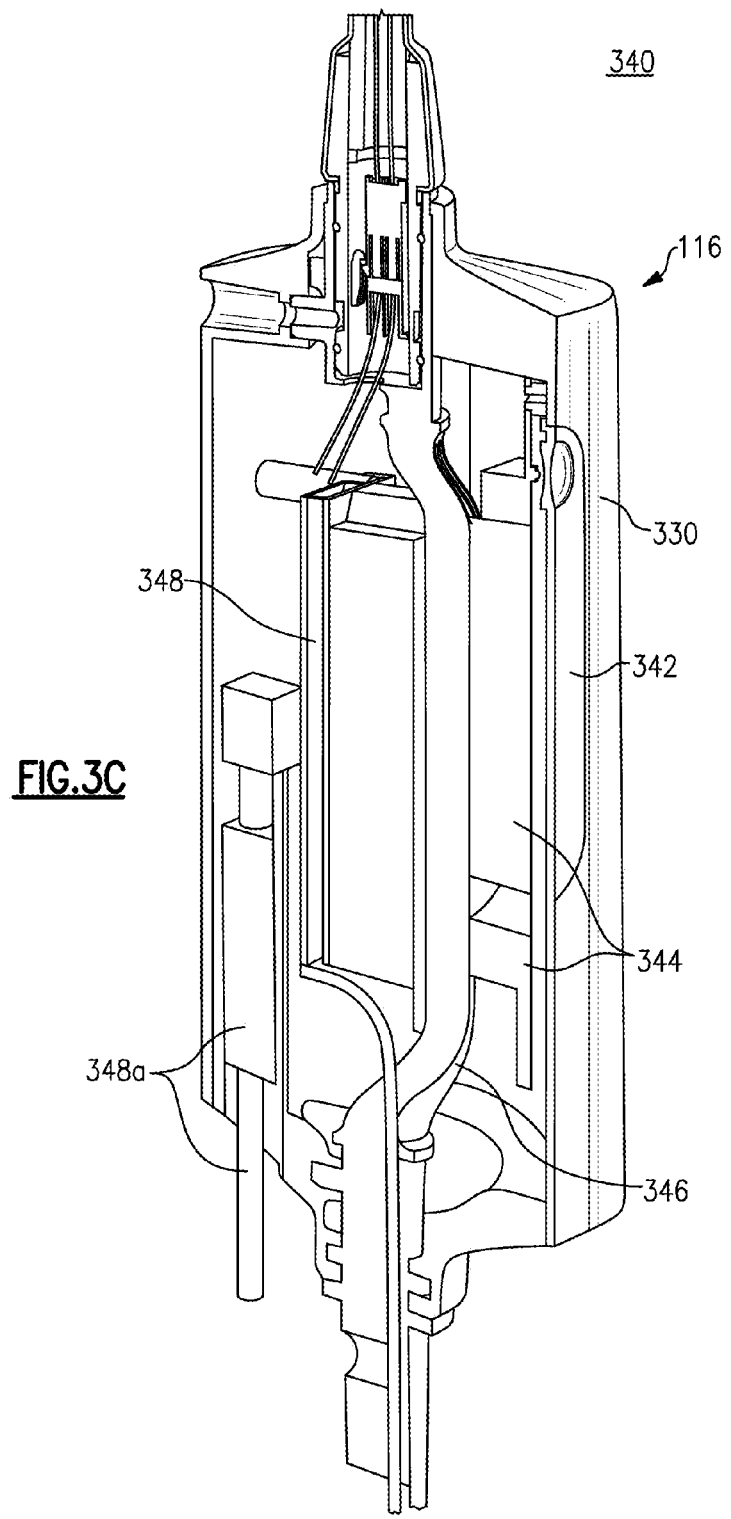

FIG. 3C illustrates a perspective cross-sectional view of the control component 116. A partial view of a front housing side and of a painted insert area 342 located on the front housing side is shown. The painted insert area 342 is recessed as part of the front housing side of the outer surface 330 of the control component 116, also referred to as the control box 116. At least one marking 332-336 (shown in FIGS. 3A-3B) is drawn into the painted insert area 342 (not shown here). A printed circuit board (PCB) 344 is attached to capacitance sensors (Shown in FIG. 4) that reside inside of the outer surface 330 and each respectively proximate to the markings within the painted insert 342. A power supply 348 and a power cable 348a a also included within the interior of the control box 116.

A metal frame 346 provides mechanical support and strength to the control component 116. The metal frame 346 has a tubular shape that is configured (designed) to mechanically interface with the upper support arm 114 and the lower support 118 so that the control component 116 can provide mechanical support to the upper support arm 114 and lamp head 112 (not shown) via its mechanical frame 346.

Figure 3D:
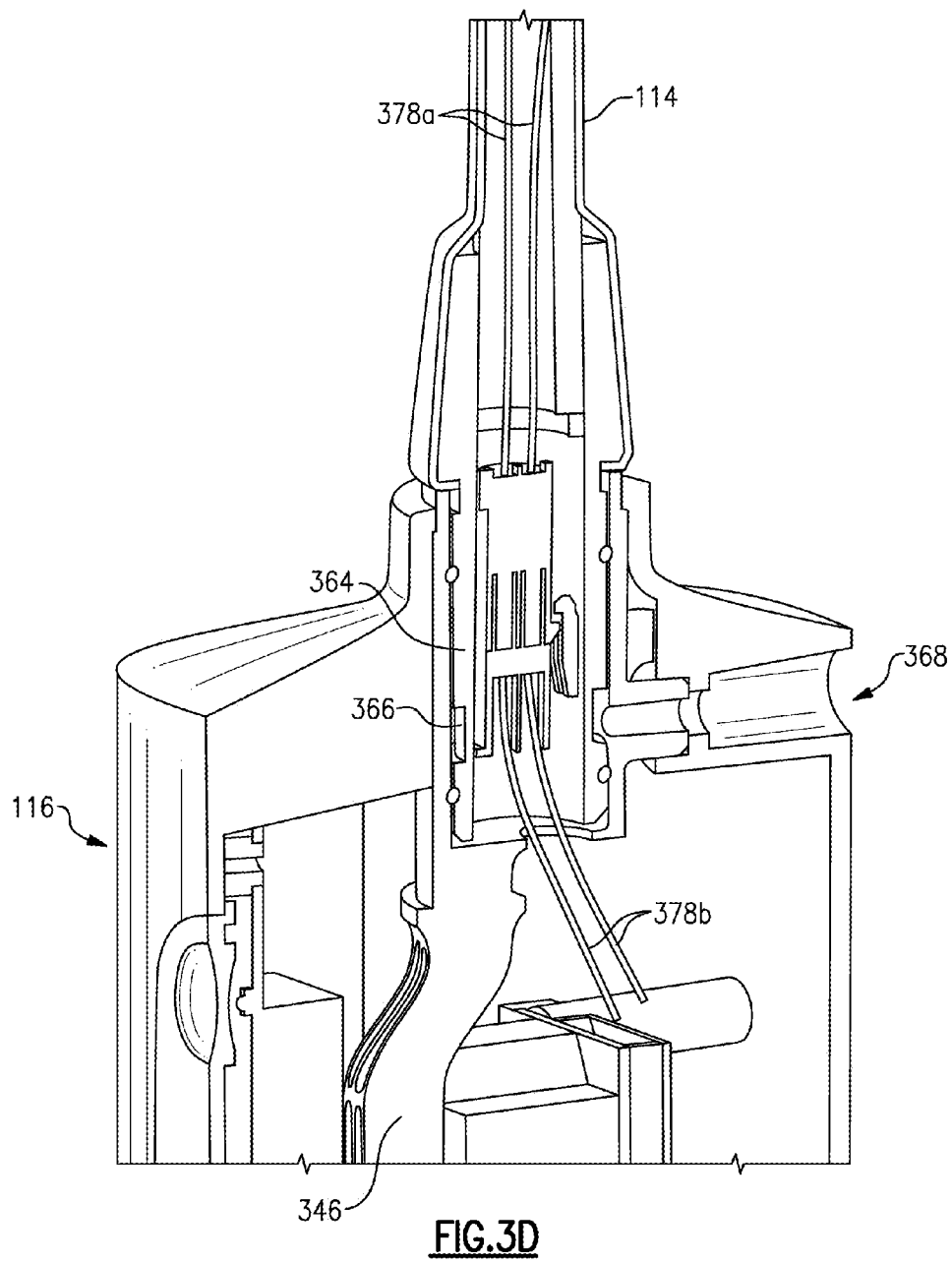

FIG. 3D illustrates a side perspective view of the a mechanical interface between the control component 116 and the upper support arm 114. As shown, a lower portion 364 of the upper support arm 114 is configured (designed) to be inserted into an upper portion of the tubular metal frame 346. The lower portion 364 includes a (2 conductor) electrical connector to electrically attach (2) conductors 378a of the upper support arm 114 (a portion of a lamp body 122) to (2) conductors 378b of the control box 116, in order to electrically attach the upper support arm 114 to the control box 116 and to form an electrical circuit between the control box 116 and the lamp head 112 that is electrically attached to the upper support arm 114 via the (2) conductors.

The lower portion 364 also includes a indented slot 366 and the control box 116 includes a passageway 368 for a screw (not shown), also referred to as a grub screw, that is designed to enter the indented slot 366, make physical contact with the lower portion 364 of the upper support arm 114 in order to attach the upper support arm 114 to the control box 116. In this embodiment, the screw within passageway 368 is turned via an allen wrench.

Figure 3E:
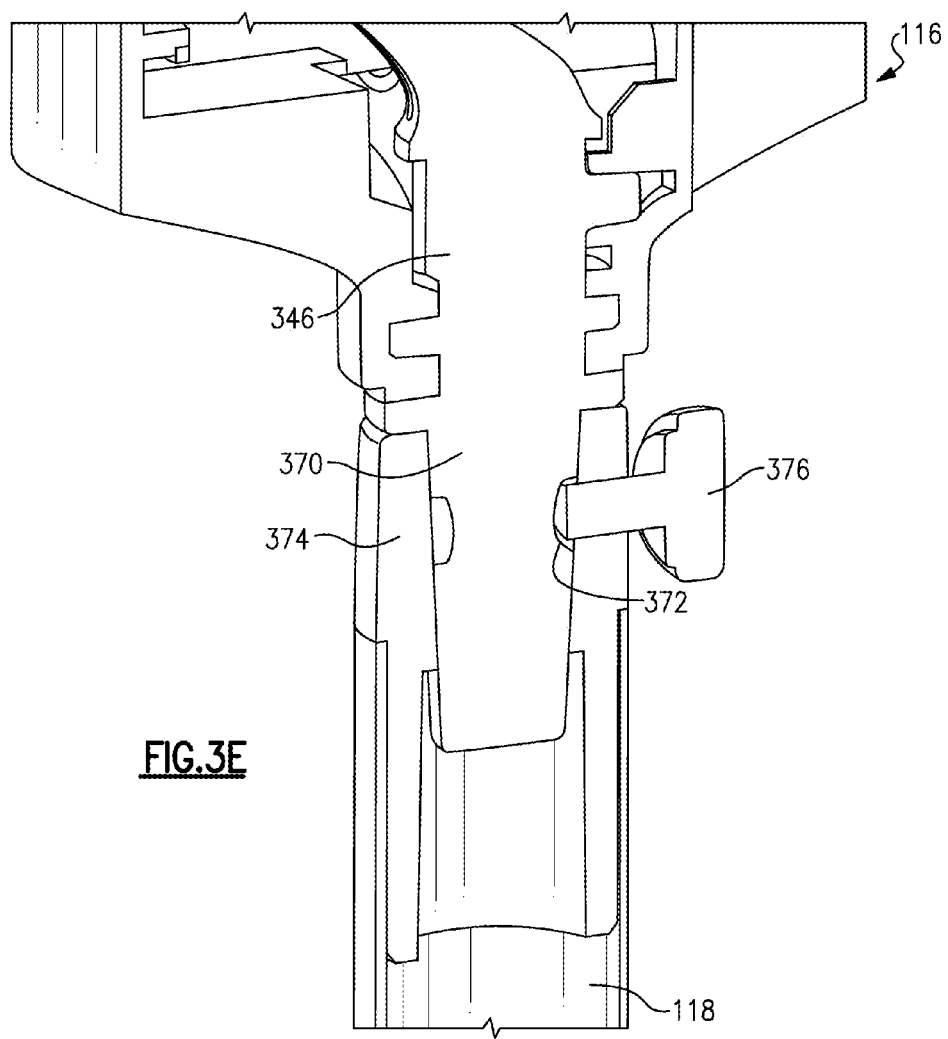

FIG. 3E illustrates a side perspective view of the a mechanical interface between the control component 116 and the lower support 118. The control box 116 also includes a protrusion 370 which includes an indented area 372. An upper portion 374 of the lower support 118 is configured to receive the protrusion 370 of the control box 116. The lower support 118 includes a passageway for and a thumb locking screw 376 that is designed to enter the indented area 372 of the protrusion 370, make physical contact with the protrusion 370 in order to attach to the lower support 118 to the protrusion 370 and the control box 116.

The design of the control box 116, enables the control box 116 to be a common component within a plurality of examination light embodiments. For example, various upper support arms 114a or 114b, each having a different attached lamp head 112a-112d, can (electrically and mechanically) attach to the control box 116. As described in association with FIG. 5, the electronic circuitry within the control box 116 adapts to the electrical requirements of the different attached lamp heads 112a-112d. Each of the lamp heads 112a-112d can have a differing arrangement and/or quantity and or type of light emitting diodes and can have correspondingly different electrical requirements. Likewise, different embodiments of the lower support 118, having differently sized wheels or no wheels at all, can also attach to the control box 116.

FIG. 4 illustrates a perspective view of the capacitance sensors 402-406 and a capacitance shield 408 that are located inside of the control component 116. Inside of (below) the outer surface 330 of the control component 116, one or more capacitance sensors 402-406 are disposed. Behind the capacitance sensors, at a further distance inside of (below) the outer surface 330 of the control box 116, a circuit board (not shown) is disposed, and behind the circuit board a capacitance shield 408 is also disposed. The circuit board includes other electronic components residing within the control component (control box) 116.

As shown, an X axis 412, a Y axis 414 and a Z axis 416 are each employed as a directional frame of reference. Each of the axes 412-416 are directed perpendicular (orthogonal to) the other (remaining) two axes. An X-Y plane (not shown) is defined as being parallel with both of the X axis 412 and the Y 414 axis. The X-Y plane is substantially parallel to a planar portion of the outer surface 330 of the control box 116 that is located where each marking 332-336 is drawn (See FIG. 3). The Z axis 416 is perpendicular to the X-Y plane and is substantially perpendicular to the planar portion(s) of the outer surface 330 where each marking 332-336 is drawn.

In this embodiment, each capacitance sensor 402-406 is implemented as an approximately (1) inch by (1) inch) square copper plate (pad), also referred to as a pad, that is employed to store an electrical charge for the purpose of sensing capacitance from sources located outside of the control box 116. Each of the pads 402-406 has a planar shape that is oriented substantially parallel to the X-Y plane and oriented substantially perpendicular to the Z axis 416.

The capacitance shield 408 also has a planar shape and is employed to shield the capacitance sensors 402-406 from sources of capacitance that are located behind the sensors and the circuit board. The capacitance shield 408 can also shield the sensors from sources of electromagnetic interference. Many of the electronic components of the control box 116 reside within the circuit board (not shown). In this embodiment, the capacitance shield 408 has a width of approximately 1.1 inches (Approximately 10% wider than each sensor) with respect to the X axis 412 and a height that is approximately 5.0 inches with respect to the Y axis 414. Like the sensors 402-406, the capacitance shield 408 is oriented substantially parallel to the X-Y plane.

Each marking 332-336 has a center point (not shown) and each sensor 402-406 has a center point (not shown). In this embodiment, the center point of each sensor 402-406 is preferably proximate to, if not aligned along the Z axis 416 with the center point of each associated marking 332-336. In other words, a line (not shown) that is parallel to the Z axis 416 and that intersects the center point of each respective marking 332-336, preferably intersects the center point of each respective sensor 402-406.

In this embodiment, each capacitance sensor 402-406 is located proximate to, approximately 0.5 inches, from its associated marking 332-336. In other words, the line (not shown) that intersects the center point of each respective marking 332-336 and of each respective sensor 402-406, is less than or equal to 0.5 inches in length between the center point of the marking 332-336 and the center point of the sensor 402-406.

Hence, the first capacitance sensor 402 is associated with and disposed proximate to marking 332, a second capacitance sensor 404 is associated with and disposed proximate to marking 334 and a third capacitance sensor 406 is associated with and disposed proximate to marking 336.

In some embodiments, each sensor 402-406 is located adjacent to the outer surface 330 of the control component 116. In this embodiment, each sensor 402-406 is located from its associated marking 332-336 by a distance approximating a thickness of the outer surface 330. In this embodiment, the thickness of the outer surface is approximately ¼ of an inch. In other embodiments, the thickness of the outer surface 330 can be reduced, to between $\frac{1}{32}$ and $\frac{1}{16}$ of an inch, to enhance capacitance sensitivity of the sensors towards entities located outside of the outer surface 330.

FIG. 5 illustrates a simplified conceptual diagram 500 of electronics residing within the control component (control box) 116. A substantial portion of the electronics shown, including the sensors 402-406 and excluding the light emitting diodes (LEDs) 226a-226c, are attached onto a circuit board that is disposed inside of the control box 116. While the capacitance sensors 402-406 are located on a forward side of the circuit board, the capacitance shield 408 is located on an opposite and rearward side of the circuit board, at a farther distance from the markings 332-336 that are drawn on the outer surface 330 of the control box 116 (See FIGS. 3-4).

As shown, a sensor activation detector 520, also referred to herein as the activation detector 520 or detector 520, includes an electrical connection 502a-506a to each of the capacitance sensors 402-406 respectively, and includes an electrical connection 508a to the capacitance shield 408. The sensor activation detector 520 also includes an electrical connection 522 to a LED control component 530. The LED control component 530 resides within a electrical circuit 560 that includes the (3) light emitting diodes (LEDs) 226a-226c and a current measuring component 550.

A power supply module 510 is configured to supply electrical power in one of two power supply embodiments. In first power supply embodiment, which is employed into the apparatus embodiment shown, a (60) watt power supply 510 is configured to supply voltage at 15 volts and at a current of up to a maximum of 4 amperes to support the power, voltage and current requirements of (1-8) LEDs. In this (apparatus) embodiment, the power supply 510 supplies power, voltage and current requirements of the (3) LEDs 226a-226c. In a second power supply embodiment, a (5) watt power supply 510 supplies voltage at 5 volts and at a current of up to a maximum of 1 ampere to support the power, voltage and current requirements of (1) LED (not shown), while the one LED is limited to projecting light at approximately half intensity (800 milliamps).

In some embodiments, a battery (not shown) is employed as a source of electrical power. Optionally, the battery is disposed at or proximate to a lower portion or the lamp body 122 and can further function as a ballast for the lamp body 122 to resist tipping of the lamp body. Optionally, the battery can be attached to a universal serial bus (USB) connection. The USB connection is designed to transfer both power and data between the battery and other electrical components. In this type of embodiment, the battery can be designed to output data indicating its status and history of use in addition to the battery outputting electrical power to other electrical components.

In this embodiment, the implementation of the sensor activation detector 520 includes a Cypress (PSoC) CY8C221534 Mixed Signal Array. The CY8C221534 Mixed Signal Array, also referred to herein as the 534 array, is a programmable component that includes configurable blocks of analog and digital logic. The activation detector 520 is configured to measure a capacitance detected by each capacitance sensor 402-406, during periodic intervals of time that are each required to perform a capacitance sampling cycle.

Each measure (sample) of capacitance at a particular time, typically represents capacitance from one or more different sources. These sources of capacitance can be divided into at least two categories, namely a source of capacitance of interest and a source of capacitance that is not of interest. Capacitance originating from an appendage (finger) of a user that is located proximate to a sensor 402-406 is a capacitance of interest, and is also referred to as foreground capacitance. Detection of foreground capacitance is indicative of a user gesturing to the apparatus 110 as a means of communicating a command to the apparatus 110. Capacitance originating from other objects and/or operating electrical components is a capacitance that is not of interest, and is also referred to as background capacitance or noise.

The activation detector 520 includes a processor, memory and software stored within its memory, that controls the operation of the processor. The software residing within the detector 520 is configured execute procedures (algorithms) that are designed for the purpose of distinguishing foreground capacitance that is of interest from background capacitance that is not of interest. Upon distinguishing a capacitance of interest, for example that capacitance originating from an appendage (finger) of a user that is proximate to a sensor for a sufficient period of time, an activation event occurs and is detected in association with that sensor 402-406. An activation event is equivalent to a button press event, but instead, this event does not necessarily involve physical contact between the user and the control box 116.

Upon occurrence of an activation event, the sensor activation detector 520 communicates one or more commands (signals) to a Light Emitting Diode (LED) control component 530 via electrical circuit communications path 522. Each command instructs the Light Emitting Diode (LED) control component 530 to adjust to and maintain a pre-determined amount of current (target current value) that passes through the LEDs 226a-226c of the lamp head 112 in order to maintain a predetermined amount of light that is to be projected from the LEDs 226a-226c. The amount of light that is projected from the LEDs 226a-226c is a function of the amount of current that passes through the LEDs 226a-226c.

In this embodiment, the Light Emitting Diode (LED) control component 530 is implemented as a Linear Technology LTC 3783 controller 530. The LTC 3783 controller 530, also referred to herein as the LED controller 530 or controller 530, is an integrated circuit (IC) that provides pulse width modulated (PWM) output for load switching.

The LED controller 520 is configured to control the amount of light that is emitted from the LEDs 226a-226c by controlling the amount of current passing through the LEDs 226a-226c. The LED control component 530 controls the amount of electrical current passing through the (3) LEDs by controlling an amount of current that is input into circuit 560. The amount of current passing through the LEDs 226a-226c is measured (monitored) via a current measuring component 550 which communicates with the LED control component 530.

In other embodiments, one "On/Off" command is communicated. In this embodiment, three commands are communicated from the sensor activation detector 520 to the LED control component 530. These (3) commands are respectively named "Off", "Half Intensity" and "Full Intensity". Upon receiving an Off command, associated with activation of sensor 402 (marking 332), the LED control component 530 shuts down and performs no further control of the current within circuit 560. As a result, current ceases to flow within the circuit 560. Upon receiving an Half Intensity command, associated with activation of sensor 404 (marking 334), the LED control component 530 sets a target current value equal to 0.8 amps (800 milliamps). Upon receiving an Full Intensity command, associated with activation of sensor 406 (marking 336), the LED control component 530 sets a target current value equal to about 1.5 amps.

In this embodiment, the electronic connection 522 is electronic circuitry that includes connections to the P0__5 (LED CONTROL) and P0__7 (LED DIM 3) pins of the 534 array, the ILIM pin of the LTC 3783 controller 530. The activation detector 520 (534 array) communicates an Off command by applying a digital low voltage signal (0.0 volts) onto its P0__5 pin, communicates a Half Intensity command by applying a digital high voltage signal onto its P0__7 pin and communicates a Full Intensity command by applying a digital low voltage signal onto its P0__7 pin.

In another embodiment that is limited to including (1) sensor, that sensor is configured to toggle between an Off and an On state. In this other embodiment, the activation detector 520 (534 array) communicates an Off command by applying a digital low voltage signal (0.0 volts) onto its P0__5 pin and communicates an On command by applying a digital high voltage signal (3.3 volts) onto its P0__5 pin.

Note that for this embodiment, a P1__4 pin (LED DIM 2) and a P1__6 pin (LED DIM 1) are each reserved for implementing future functionality, including current control. Each of the pins of the 534 array that can be used for current control, such as the P0__7, P1__4 and P1__6 pins, is connected to a separate transistor (not shown) that is configured to turn on when a high voltage signal is applied to its associated pin of the 534 array and configured to turn off when a low voltage signal is applied to its associated pin.

When turned on, each respective transistor allows other current, not sourced from the associated pin of the 534 array, to flow to ground through a respective set of resistors that are each arranged to function as a voltage divider. Each voltage divider causes a different voltage to be applied to the ILIM pin of the LTC 3783 controller 530. The LTC 3783 controller is configured so that an amount of voltage applied to the ILIM pin signals to the LTC 3783 controller 530, an amount of current (target current) to be sought and maintained (controlled) by the LTC 3783 controller. When the P0__5 pin is turned off, the LED control component 530 shuts down and the voltage applied to the ILIM pin of the LTC 3783 controller 530 has no effect.

The LED control component 530 includes current control circuitry that is configured to control (adjust) and maintain a target amount of current that flows through circuit 560. In this embodiment, the current control circuitry outputs a pulse width modulated (PWM) signal at approximately 260 kilohertz through the GATE pin of the LTC 3783 controller 530. This signal is a square wave signal having an ON duty cycle and an OFF duty cycle. During the ON (high voltage) portion of the square wave, a field effect transistor (FET) is turned ON. During the OFF (low voltage) portion of the square wave, the FET is turned OFF.

The FET is configured to intercept and re-direct current flowing out of an inductor and flowing into (2) rectifier diodes and into the circuit 560. When the FET is turned ON during a period of time of the ON portion (duty cycle) of the PWM signal, it intercepts and re-directs the current that is output from the inductor, to ground and away from the (2) rectifier diodes and away from the circuit 560. When the FET is turned OFF during a period of time of the OFF portion (duty cycle) of the PWM signal, it ceases intercepting and re-directing current output from the inductor to ground, and instead allows the current to again flow through the (2) rectifier diodes and into the circuit 560. Down stream of the (2) rectifier diodes, a plurality of capacitors are employed to smooth current and voltage transients caused by the small bursts of current passing through the (2) rectifier diodes and into the circuit 560.

When the FET is turned ON, current drains to ground and causes an accelerated flow of current into the inductor. When the FET is then turned off, current bursts from the inductor and through the (2) rectifier diodes and into the circuit 560. As a result, the longer the ON duty cycle and the shorter OFF duty cycle, the larger the burst of current that is later output from the inductor into the circuit 560. Conversely, the shorter the ON duty cycle and the longer the OFF duty cycle, the smaller the burst of current that is later output from the inductor into the circuit 560.

The LED control component 530 includes voltage buck/boost circuitry 540 that is configured to buck or boost voltage that is input from the power supply 510 and that is output to the circuit 560. In this embodiment, the power supply 510 supplies electrical power at 15 volts and up to a maximum of 4 amperes. Depending upon the design of a particular embodiment, including the design of a LED configuration, the voltage that is required to be output from the voltage buck/boost circuitry 540 can be of a higher or lower value than the 15 volts supplied by the power supply 510.

Each LED 226a-226c has an input electrode and an output electrode. During normal LED operation, up to 1.5 amps of current flows through each LED 226a-226c. Current flows through each LED 226a-226c by flowing into its input electrode and flowing out of its output electrode. The normal operation of each LED 226a-226c causes approximately a 4 volt drop between its input electrode and an output electrode. Hence electrical power of approximately 12 volts at up to 1.5 amps is required to be provided to power (3) LEDs 226a-226c that are connected in series, within circuit 560.

Consequently, in this embodiment that uses a (15) volt power supply 510, the voltage buck/boost circuitry 540 bucks the voltage input from the power supply 510 to the circuit 560 from 15 volts to approximately 12 volts, during normal operation of the (3) LEDs 226a-226c. For the (1) LED embodiment (not shown), the voltage buck/boost circuitry 540 bucks the voltage input from the (15) volt power supply 510 to the circuit 560 from 15 volts to approximately (4) volts, during normal operation of the (1) LED (not shown).

The electronics of FIG. 5 are configured to support a variable quantity of LED's ranging from (1-8) LEDs. The circuit 560 requires a voltage differential of the number of LEDs multiplied by approximately (4) volts per LED included within the circuit 560. Hence, a (4) LED configuration requires approximately (16) volts, a (5) LED configuration requires approximately (20) volts, a (6) LED configuration requires approximately (24) volts, a (7) LED configuration requires approximately (28) volts and an (8) LED configuration requires approximately (32) volts.

Consequently, in this embodiment that employs a (15) volt power supply 510, for configurations of (1-3) LEDs, the buck/boost circuitry 540 bucks voltage from the (15) volt power supply 510 to that required for normal operation of the (1-3) LEDs employed within the circuit 560. For configurations of (4-8) LEDs, the buck/boost circuitry 540 boosts voltage from the (15) volt power supply 510 to that required for the (4-8) LEDs that are employed within the circuit.

In other embodiments, a (5) volt and (5) watt power supply 510 is instead employed, and the circuit 560 is limited to including (1) LED and the voltage buck/boost circuitry 540 would to buck the circuit 560 voltage from (5) volts to approximately (4) volts, as required for the (1) LED.

The LED control component 530 also interfaces with a current measuring component 550 via an electronic connection 552. A current measuring component 550 is configured to measure an amount of current passing through the circuit 560. In this embodiment, the current measuring component 550 includes a resistor that resides in series within the circuit 560 and that has a predetermined and fixed resistance value. The difference in voltage across the resistor, between an input and output electrode (terminal) of the resistor, is proportional to the amount of current passing through the resistor, in accordance with the relationship between voltage, current and resistance (V=IR).

In this embodiment, the electronic connection 552 includes electronic circuitry that communicates a input voltage at the input electrode and an output voltage at the output electrode of the resistor having a fixed and predetermined resistance value, to the LTC 3783 controller of the LED control component 530. The input voltage and the output voltage of the resistor are each respectively applied to the FBN and FBP pins of the LTC 3783 controller 530.

The LED control component 530 employs the current measuring component 550 as a feedback mechanism for controlling the current that is output by the current control circuitry of the LED control component 530. After a target current is set via receipt of a command from the sensor activation detector 520, the LED control component 530 operates to maintain an amount of current passing through the LEDs 226a-226c to be equal to the target current.

For example, in one operational scenario, the sensor activation detector 520 detects the activation of the sensor 404 and communicates a "Half Intensity" command to the LED control component 530 via electronic connection 522. In response, the LED control component 530 sets a target electrical current amount equal to approximately (about) 800 milliamps (0.8 amps) and continuously measures the actual current flowing through the circuit 560 via the current measuring component 550. If at the time of the communication of the "Half Intensity" command, the actual current flowing through circuit 560 is equal to 0.8 amps, no immediate action is performed by the LED control component 530.

If at the time of the communication of the "Half Intensity" command, the actual current flowing through the circuit 560 is lower than 0.8 amps, the LED control component 530 sends a signal to the current control circuitry to raise the actual amount of current flowing in the circuit 560. The LED control component 530 re-measures the actual current via the current measuring component 550 and if necessary, adjusts the PWM signal it is applying to the GATE pin of the LTC 3783 controller.

To raise current, the PWM ON duty cycle portion of the square wave signal is lengthened and the PWM OFF duty cycle portion of the square wave signal is reduced. This signal modification increases the amount of current directed to the inductor and raises the amount of current flowing into the (2) rectifier diodes and into the circuit 560, during the time of each square wave cycle. These current measuring and current adjustment actions are repeated in an iterative fashion until the actual current is equal to the target current value of 0.8 amps.

If at the time of the communication of the "Half Intensity" command, the actual current flowing through the circuit 560 is higher than 0.8 amps, the LED control component 530 sends a signal to the current control circuitry to lower the actual amount of current flowing in the circuit 560. The LED control component 530 re-measures the actual current via the current measuring component 550 and if necessary, adjusts the PWM signal it is applying to the GATE pin of the LTC 3783 controller.

To lower current, the PWM OFF duty cycle portion of the square wave signal is expanded in length over time and the PWM ON duty cycle portion of the square wave signal is reduced in length over time. This signal modification reduces the amount of current directed to the inductor and lowers the amount of current flowing into the (2) rectifier diodes and into the circuit 560, during the time of each square wave cycle. These current measuring and current adjustment actions are repeated in an iterative fashion until the actual current is equal to the target current value of 0.8 amps.

The sensitivity of the capacitance sensors 402-406 is adjusted via a resistor within circuitry connected to the Cypress 534 array P0__1 and P1__5 pins. In this embodiment, this circuitry includes a resistor that has a resistance value of approximately 2 Kohms. In other embodiments, difference resistance values can be employed to effect a different level of sensitivity of the capacitance sensors 402-406.

FIGS. 6A-6C each illustrate a set of (3) capacitance count values that are obtained in association with each of the (3) capacitance sensors 402-406 during a cycle. A capacitance that is obtained in association with each sensor 402-406 during a cycle, is represented by the activation detector 520 in terms of a numerical value, also referred to as a capacitance count value or a count value. A capacitance count value that is obtained (sampled) in association with a sensor 402-406 is monotonically related to a capacitance detected via that sensor 402-406. In other words, the higher the capacitance count value that is obtained (sampled) by the activation detector 520 in association with a sensor 402-406, the higher the capacitance that is detected via that sensor 402-406.

The software residing within the detector 520 is configured for detecting a presence of capacitance, such as capacitance from a finger of the user that is proximate to a sensor 402-406, representing (constituting) an activation event. To detect such an activation event, the activation detector 520 obtains a capacitance count value in association with each sensor 402-406 during each cycle.

In this embodiment, a cycle is performed within a 30-35 millisecond period of time and a capacitance count value is sampled (obtained) for each sensor 402-406 within that period of time. Hence, the activation detector 520 obtains about 30 capacitance count samples (count values) per sensor 402-406 per second. Each capacitance count value that is obtained (sampled) by the activation detector 520 is stored into memory and further processed by the activation detector 520. The capacitance count value is stored in a 15 bit value and a maximum capacitance count value is equal to a value of about 32,767.

FIG. 6A is a bar chart graph representing a first set of (3) capacitance count values respectively obtained for sensors 402-406 during a first cycle (sample) occurring during a first periodic time interval. As shown, a capacitance count value that is obtained for sensor 402 is equal to approximately 17200, a capacitance count value that is obtained for sensor 404 is equal to approximately 20,800 and a capacitance count value that is obtained for sensor 406 is equal to approximately 18500. The relative amount of capacitance detected is the highest for sensor 404 and the lowest for sensor 402.

FIG. 6B is a bar chart graph representing a second sample of (3) capacitance count values obtained for sensors 402-406 during a second cycle (sample) occurring during a second periodic time interval. As shown, a capacitance value that is obtained for sensor 402 is equal to approximately 19500, a capacitance value that is obtained for sensor 404 is equal to approximately 17,500 and a capacitance value that is obtained for sensor 406 is equal to approximately 20,100. The relative amount of capacitance detected is the highest for sensor 406 and the lowest for sensor 404.

FIG. 6C is a bar chart graph representing a third sample of (3) capacitance count values obtained for sensors 402-406 during a third cycle occurring during a third periodic time interval. As shown, a capacitance value that is obtained for sensor 402 is equal to approximately 19700, a capacitance value that is obtained for sensor 404 is equal to approximately 18,500 and a capacitance value that is obtained for sensor 406 is equal to approximately 17,300. The relative amount of capacitance detected is the highest for sensor 402 and the lowest for sensor 406.

Typically, each obtained capacitance count value represents capacitance that includes a substantial amount of capacitance that is not of interest. In many circumstances, a capacitance count value entirely represents capacitance that is not of interest. In some circumstances, that capacitance includes some amount of capacitance that is of interest, possibly representing an activation event.

Capacitance that originates from a finger of the user that is located proximate to a sensor 402-406, is classified as foreground capacitance, and is of interest. Capacitance that is from other objects and/or operating electrical components, is classified as background capacitance (noise) and is not of interest.

For example, with respect to the hardware configuration of the current embodiment, an typical amount of background capacitance would register in the range of 17,000-23,000 capacitance counts. A typical foreground capacitance of a finger touching the marking 332-336 associated with a sensor would typically register (add) approximately 300 capacitance counts to the background capacitance. A finger that is located within (1) inch of the marking 332-336 would typically register (add) (100) capacitance counts. A finger that is located approximately (2) inches away from the marking 332-336 would typically register (add) (20) capacitance counts. As a result, searching through raw capacitance measurements over time to separate foreground capacitance from background capacitance from the raw that is measured by the sensors 402-406 can be like searching for a needle in a hay stack.

Capacitance, whether it is classified as background or foreground capacitance, that is detected by each sensor 402-406 can vary for each sensor 402-406 over time and can vary between sensors 402-406 at a particular time. Furthermore, a relative amount of capacitance that is detected by each sensor 402-406 at a particular time, meaning an amount of capacitance that is detected by a sensor 402-406 relative to an amount of capacitance detected by other sensors 402-406 at that particular time, can vary over time. For example, because the apparatus 110 is portable, movement of the apparatus 110 can cause capacitance detected by each sensor 402-406, and the relative amount of capacitance detected by each sensor, to vary by location of the apparatus 110 during movement of the apparatus 110 over time. For example, the background capacitance count values raise when the apparatus 110 becomes proximate to a wall, where proximity to a wall can cause a substantial amount of background capacitance to be detected by the sensors 402-406. Movement of other equipment, within the environment employing the examination light, such as within a health care environment, can also have substantial and varied effects upon background capacitance count values detected by each of the sensors 402-406.

FIG. 7 illustrates a simplified and conceptual diagram of the operation of software that executes within the sensor activation detector 520. The activation detector 520 is configured to process and interpret the capacitance values over time in order to detect a presence of capacitance that represents an activation event. Upon power on and initialization of the activation detector 520, a first (capacitance sampling) cycle is performed that is referred to as cycle number (1) or cycle (1), the next cycle performed is cycle (2) etc.

As shown, an Initiate Cycle step 710 initiates a cycle. This step performs various and miscellaneous initial operations apart from operations specifically shown and described in this figure. During a cycle, a capacitance count is obtained for each sensor 402-406. Each capacitance count obtained can represent capacitance from background (not of interest) and/or foreground (of interest) sources of capacitance. At step 712, a short term moving average (STMA) is computed for each and every sensor 402-406. At step 714 and a long term moving average (LTMA) is computed for each and every (all) sensor 402-406. The STMA and the LTMA are computed based upon a capacitance count obtained during each cycle, including the current cycle and prior cycles.

In this embodiment, the STMA is computed to be equal to the average capacitance count obtained from (8) consecutive cycles. The STMA has a computation frequency equal to every (1) cycles, meaning that it is computed in each and every cycle. During each cycle, the consecutive (8) capacitance count values (samples) for each sensor 402-406 are averaged into one STMA value, that is computed for that cycle, for each and every respective sensor 402-406. Hence, the STMA is computed to equal the average of the capacitance count obtained from the current cycle and of the capacitance count values obtained from (7) other prior and consecutive cycles, for each and every respective sensor 402-406.

For example, in cycle number (8), the short term moving average (STMA) is equal to the average capacitance count obtained from the current and prior (7) cycles, specifically cycles (1) through (8), for each respective sensor 402-406. In cycle number (9), the short term moving average is equal to the average capacitance count obtained from the cycles (2) through (9). In cycle (10), the short term moving average is equal to the average capacitance count obtained from the cycles (3) through (10).

A long term moving average (LTMA) is not necessarily computed each and every cycle, but is instead periodically computed within certain cycles. In this embodiment, the LTMA is computed during every (5th) cycle. Hence, the LTMA has a computation frequency of every (5) cycles. To compute the LTMA, a short term moving average that is computed for every (5th) cycle is stored and averaged with the short term moving average computed for cycles that were (5), (10), (15), (20), (25), (30), (35) and (40), cycles prior to the current cycle, yielding a long term average that is computed for and during the current cycle, for each respective sensor

402-406. For example, in cycle number (80), the long term moving average (LTMA) is equal to the average of the short term average (STMA) that was computed in cycle numbers (80), (75), (70), (65), (60), (55), (50) and (45). In cycle number (85), the long term moving average (LTMA) is equal to the average of the short term average (STMA) that was computed in cycle numbers (85), (80), (75), (70), (65), (60), (55) and (50).

There are other possible means of calculating a LTMA. In the current embodiment the LTMA is not calculated every cycle so that during cycle numbers (86), (87), (88), and (89) the LTMA remains what it was calculated to be during cycle number (85). This reduces the computational resources needed without substantially degrading the usefulness of the LTMA. Other embodiments may compute the LTMA every cycle using values of the STMA that were stored during each of the preceding cycles extending back some period of time. In such a case the LTMA calculated during cycle number (86) would equal to the average of the STMA that was computed in cycle numbers (86), (81), (76), (71), (66), (61), (56), and (51).

In step 716, during each cycle, a moving average difference value (MADV) is computed for each and every sensor 402-406. A moving average difference value (MADV), is equal to a difference between the value of the currently computed STMA and the value of the currently computed LTMA, for each respective sensor 402-406, during each cycle. Computing an MADV is useful as a preliminary step for detecting an activation event, for example caused by an appendage (finger) of a user that is proximate to a sensor 402-406 for a sufficient period of time. Via the computation of an MADV for each sensor 402-406, the activation detector 520 monitors a mathematical relationship between the STMA and the LTMA for each sensor 402-406, during each cycle, over time.

In step 720, an MADV that was computed for each sensor 402-406 is compared against a threshold value associated with each sensor 402-406. If for a particular sensor 402-406, a computed current MADV is positive, meaning that the current STMA is greater than the current LTMA for that sensor 402-406, and if the current MADV exceeds a predetermined threshold value associated with that sensor 402-406, also referred to as an initial threshold value, then that sensor 402-406, is identified (flagged) as a candidate for receiving an associated activation event.

Because the sensors 402-406 each have a relative sensitivity for detecting capacitance, based upon their location relative to each other, relative to other sources of background capacitance and relative to a source of foreground capacitance, such as the anatomy of the human hand when attempting to activate a sensor 402-406, the threshold value for each sensor 402-406 is not necessarily equal in value for each and every sensor 402-406, and instead is a value that can be customized (unique) to each sensor 402-406.

For example, in this embodiment, the initial threshold value for sensor 406 is equal to 15 capacitance counts, the initial threshold value for sensor 404 is equal to 23 capacitance counts and the initial threshold value for sensor 402 is equal to 20 capacitance counts.

If in step 720, if at least one sensor 402-406 is identified (flagged) as an activation candidate sensor, the MADV for the activation candidate sensor is further compared against the MADV computed for each of the other sensors 402-406, in step 730. Else if in step 720, no sensor is identified (flagged) as an activation candidate sensor, then the software execution transitions to step 770 (Optionally Adjust LTMA Compute Frequency and/or Reset LTMA Values) which is described in further detail near the end of the description of FIG. 7.

Referring to step 730, in some circumstances, one or more of the sensors 402-406 may also have an associated MADV that each exceed an associated initial threshold associated with that respective sensor 402-406 during the current cycle. The MADV for each sensor that has a MADV above its initial threshold is compared to the MADV of the other sensors in an effort to discriminate between background and foreground capacitance sources and to reject noise. The differences between MADVs provide information not obtained by examining each MADV independently. By comparing the differences in MADVs it is determined if an activation candidate sensor is detecting a capacitance source of the correct size, shape, and orientation to warrant a partial activation event. If the MADV of one activation candidate sensor compares favorably to the MADV computed for each of the other sensors 402-406, then the activation candidate sensor is further identified (flagged) as receiving a partial activation event count during this current cycle, and is further identified (flagged) as a lead activation candidate sensor. To compare favorably relative to the other (2) sensors 402-406, the MADV of the activation candidate sensor falls within an acceptable range of difference (AROD) relative to the MADV of the other two sensors 402-406.

The AROD value represents the extent that a capacitance source should interact with the sensors adjacent to the sensor that it is closest too. When a capacitance sources moves toward a sensor it also may, to a lesser degree, move closer to other sensors. The size and shape of the capacitance source affects the rise in the MADVs of the adjacent sensors relative to the rise of the MADV of the sensor closest to the capacitance source. The AROD values allow discriminating against capacitance sources that do not correctly interact with adjacent sensors.

In this embodiment, the AROD values were determined through empirical testing to accept a human hand with a finger extended. For example, if the activation candidate sensor is sensor 406, the acceptable range of difference (AROD) between the MADV of sensor 406 and the MADV of sensor 404, is −4 capacitance counts and higher. In other words, if the MADV of sensor 406 is greater than the MADV of sensor 404 minus 4 capacitance counts, then the sensor 406 compares favorably to sensor 404. The acceptable range of difference (AROD) between the MADV of sensor 406 and the MADV of sensor 402, is 0 and higher. In other words, if the MADV of sensor 406 is greater than or equal to the MADV of sensor 402, then sensor 406 compares favorably to sensor 404.

These comparisons check that the activation candidate sensors MADV has increased to an extent large enough relative to the adjacent sensors. Other embodiments may also check that the MADV has not increased by too much relative to the adjacent sensors. An activation candidate sensor must have a MADV that when compared to the MADV of other sensors falls within the AROD that has been set for each of the comparisons.

Like the initial threshold value for each sensor 402-406, the AROD associated with each sensor 402-406 may not be the same for each sensor 402-406. Because the sensors 402-406 each have a relative sensitivity for detecting capacitance, based upon their location relative to each other, relative to other sources of background capacitance and relative to a source of foreground capacitance, such as the anatomy of the human hand when attempting to activate a sensor 402-406, the AROD for each sensor 402-406 is not necessarily the same (equal) for each and every sensor 402-406, and instead can be customized (unique) to each sensor 402-406.

In addition to independently choosing the AROD for each sensor the comparison of MADVs may contain multiplying coefficients or other variations to counteract dynamic differences in the sensitivity between the sensors. The differences in sensitivity, caused by printed circuit board layout, component placement, the shape of the enclosure, and other unknown parameters, can be determined through testing and considered during comparison of the MADVs.

In step 740, if the MADV of a sensor, such as sensor 406, compares most favorably relative to the MADV that is computed for the other sensors 402-404, then that activation candidate sensor 406 is further identified (flagged) as receiving (being assigned) a partial activation event count during this cycle and is further identified (flagged) as a lead activation candidate sensor, and the software execution transitions to step 750. Else if no sensor 402-406 compares most favorably relative to the MADV that is computed for the other (2) sensors 402-406, then no sensor 402-406 is flagged as receiving (being assigned) a partial activation event count during this cycle and no sensor 402-406 is further identified (flagged) as a lead activation candidate sensor and the software execution transitions to step 770 (Optionally Adjust LTMA Compute Frequency and/or Reset LTMA Values) which is described in further detail near the end of the description of this figure.

In step 750, a partial activation event count is incremented for each consecutive cycle that one same lead activation candidate sensor is identified (flagged) as receiving a partial activation event count. If in this cycle, a lead activation candidate sensor receives a partial activation event count during a pre-determined number of consecutive cycles, then a full activation event is identified (flagged) and assigned to (associated with) the lead activation candidate sensor and software transitions to step 760. In this embodiment, the pre-determined number of consecutive cycles equals (10) consecutive cycles. The pre-determined number of consecutive cycles can be set to a higher or lower value in other embodiments. Else if during this cycle, no partial activation event is received for the lead activation candidate of the prior cycle, any prior consecutive series of prior partial activation event counts for the lead activation candidate of the prior cycle is thereby terminated and no full activation event is identified (flagged) during this cycle.

In step 760, upon identification (detection) of a full activation event in response to detecting (10) consecutive partial activation events, the user selection (effectively a button press of the lead activation candidate sensor) is detected by the software and appropriate action is taken associated with the lead activation candidate sensor 402-406. In this embodiment, upon detecting a full activation event, partial activation events are not counted and detection of another full activation event is not initiated during the next (15) cycles. The period for counting partial activation events is also referred to as the partial activation period.

In this embodiment, one of three commands can be communicated from the sensor activation detector 520 to the LED control component 530. If the lead activation candidate sensor is sensor 406, then a Full Intensity command is communicated to the LED control component 530. If the lead activation candidate sensor is sensor 404, then a Half Intensity command is communicated to the LED control component 530. If the lead activation candidate sensor is sensor 402, then an Off command is communicated to the LED control component 530. The software execution transitions to step 770 (Optionally Adjust LTMA Compute Frequency and/or Reset LTMA Values) described below.

In step 770, parameters associated the computation of the LTMA values for each sensor 402-406 are optionally adjusted. If the LTMA is greater than the STMA for each sensor 402-406 for a predetermined consecutive number of cycles, then the computation frequency of the LTMA is adjusted to compute the LTMA more frequently. In this embodiment, the computation frequency is adjusted from being computed in every (5) cycles to every (1) cycle. This parameter change enables the lower STMA to have a faster acting influence upon the higher LTMA in order to lower the LTMA in less time, over time.

In step 770, upon transitioning from step 760, a detection of a full activation event in this cycle, the current LTMA value for each sensor 402-406 is reset to another value, that could be lower or higher than the current LTMA value, based upon the current STMA value for each sensor 402-406. This reset operation sets an initial (post full activation event) LTMA value for each sensor to better prepare the software for detecting the next partial and/or full activation event associated with that sensor.

Referring back to step 720, during a period of time including a series of (10) consecutive cycles where a partial activation count is being tallied (counted) in step 750, the value of the LTMA, which is computed based upon the value of the STMA for each cycle, has a tendency to raise towards the value of the STMA, because the STMA is being raised in response to the presence of foreground capacitance that is being detected as one or more partial activation events. If the threshold value were a fixed constant through out the (10) consecutive cycles, there is a risk that the MADV of the first candidate sensor 402 might not exceed its threshold value during a cycle occurring within the (10) consecutive cycles following the assignment of the first partial activation event, even though a finger of the user remains stationary and proximate to the lead activation candidate sensor.

The above described risk of using a constant threshold value applies when a finger of the user remains stationary at a fixed location over the (10) consecutive cycles. In a variation of this scenario, this type of risk is increased when the user is intending to activate the sensor but where the finger of the user moves slightly away from the sensor during the (10) consecutive cycles. This type of slight finger motion can cause an intermittent, but not a sufficiently consecutive, set of one or more partial activation events, that cause a false negative detection of an full activation event (foreground capacitance) that was intended by the user.

To address the above describe scenario risks, upon a first partial activation event count being assigned to a sensor 402-406, the MADV threshold value for that sensor is lowered in value during the determination of each consecutive partial activation event count for that sensor during at most, the series of (10) consecutive cycles following the assignment of the first partial activation event, or until a partial activation event is not assigned during a cycle for that sensor 402-406 during the series of (10) consecutive cycles following the assignment of the first partial activation event.

To lower an MADV threshold, each threshold value is reduced by subtracting a threshold reducing value (TRV) during at least some of the (9) consecutive cycles that follow the first partial activation event cycle. In this embodiment, the threshold reducing value is constant, has a value of (6) capacitance counts, and is subtracted during each of the (10) consecutive cycles. In other embodiments, the threshold reducing value is dynamic and increases in value over time during the (10) consecutive cycles, following the assignment of the first partial activation event.

Referring back to step 760, upon detection of a full activation event, the amount of background (noise) capacitance that is detectable by the sensors 402-406 is subject to substantially change upon taking the appropriate action in response to that event. For example, when transitioning from the OFF to the Half Intensity or the Full Intensity states of operation, electrical activity on the circuit board and an amount of sensor detectable background capacitance (noise) raises substantially. Conversely, when transitioning from the Full Intensity to Half Intensity or the OFF state of operation, electrical activity on the circuit board and an amount of sensor detectable background capacitance (noise) lowers substantially.

The above described substantial raise of background noise creates a risk of a false positive detection of a sensor activation event. The above described substantial lowering of background noise creates a risk of a false negative detection of a sensor activation event. To, address this risk, in response to detection of a full activation event, the long term moving average (LTMA) value is reset to a value that is dependent (based) upon the short term moving average (STMA) value.

In this embodiment, which employs the (3) LEDs 226a-226c, the LTMA is set to the STMA in response to detection of a full activation event, with no further adjustments. In another embodiment, employing (1) LED that is located where marking 332 is shown (See FIG. 3), the LTMA is set to the STMA plus post activation correction value (PACV) equal to (16) capacitance counts.

The above values, including the moving average difference value (MADV) threshold, the acceptable range of difference (AROD), the threshold reducing value (TRV), and the post activation correction value (PACV) for each sensor 402-406 can be determined and adjusted through empirical testing (trial and error) of a particular hardware configuration. Each hardware configuration has is own particular design characteristics and operating idiosyncrasies. The values specified for this embodiment were determined in an empirical (trial and error) fashion for a particular hardware design configuration, and are subject to be further adjusted (optimized/tuned) over time in pursuit of better (more reliable) test results. Better (more reliable) test results raise the likelihood of true positives and true negatives and lower the likelihood of false positives and false negatives, with respect to the detection of an occurrence of a user intended sensor activation event, such as the user positioning a finger sufficiently proximate to a sensor 402-406.

To summarize, the invention provides for a device having a control component including an outer surface. The control component including at least one electrical capacitance sensor that is located behind the outer surface and wherein control of the device is exercised by positioning a human appendage within proximity of the electrical capacitance sensor without requiring the appendage to make physical contact with said outer surface of said control component. Optionally, the outer surface includes no moving parts, excludes surface pockets and is configured to form a barrier between inner portions of said control component and contamination that could be deposited upon said control component via physical contact between a user and said control component. In some embodiments, the proximity is one inch or less from the sensor. In other embodiments, the proximity is 0.75 inches or less from the outer surface. In other embodiments, the proximity is two inches or less from the sensor.

In some embodiments, the device includes a first electrical capacitance sensor that is configured to be toggled to transition operation of said device to between and ON and an OFF state. In some embodiments, the device includes digital logic that is configured to discriminate between background and foreground capacitance using procedures that compute at least one moving average of an amount of capacitance that is detected over time by a electrical capacitance sensor.

The invention also provides for a system and method of making a device including the steps of providing a control component including an outer surface. The control component also including at least one electrical capacitance sensor that is located behind the outer surface and wherein control of the device is exercised by positioning a human appendage within proximity of the electrical capacitance sensor without requiring the appendage to make physical contact with said outer surface of said control component. Optionally, the outer surface includes no moving parts, excludes surface pockets and is configured to form a barrier between inner portions of said control component and contamination that could be deposited upon said control component via physical contact between a user and said control component.

The invention also provides for an examination lamp apparatus that is controlled without requiring physical contact from a user. The apparatus includes a lamp head that is configured to project light, a lamp body that is configured to electrically attach to and physically support the lamp head, a lamp control component that includes an outer surface and that is configured to enable a user to control an amount of light that is projected from the lamp head without requiring physical contact between the user and the lamp control component. The control component includes at least one electrical capacitance sensor located behind the outer surface and where the control is exercised by positioning a human appendage within near proximity of the electrical capacitance sensor without the appendage making physical contact with the outer surface of the control component. In some embodiments, the proximity is one inch or less. In other embodiments, the proximity is 0.75 inches or less. In other embodiments, the proximity is two inches or less.

In some embodiments, the outer surface of the lamp control component includes no moving parts, excludes surface pockets and is configured to form a barrier between inner portions of the lamp control component and contamination that could be deposited upon the lamp control component via physical contact between a user and the lamp control component. At least one electrical capacitance sensor is disposed inside of and proximate to a portion of the outer surface of the lamp control component, and wherein the electrical capacitance sensor is further configured to detect a capacitance of an appendage of a user being placed in physical contact with or within near proximity of, the portion of the outer surface of the lamp control component.

In some embodiments, the examination lamp apparatus includes a variable quantity one or more light emitting diodes. Optionally, the examination lamp apparatus includes an LED control component that is configured to adapt to and supply an amount of electrical power, voltage and current to the variable quantity of light emitting diodes, in accordance with electrical power requirements of the variable quantity of light emitting diodes. Optionally, the LED control component is further configured to supply an amount of electrical power, voltage and current to the variable quantity of light emitting diodes in accordance with the amount of light controlled by the user.

In some embodiments, the lamp body is configured to electrically attach to one of a plurality of lamp heads that each include a unique arrangement and quantity of light emitting diodes, and where the LED control component is configured to adapt to and supply an amount of electrical power, voltage and current to the one of the plurality of lamp heads upon electrical attachment between the lamp body and the one of the plurality of lamp heads.

In some embodiments, the lamp head power supply component is supplied electrical power from a battery. Optionally, the battery is further employed as a ballast for the examination light apparatus. Optionally, the battery is configured to be attached to a universal serial bus so that status and use history of the battery can be obtained by other components within the examination light apparatus. In some embodiments, the examination lamp apparatus includes a first electrical capacitance sensor that is configured to be toggled to transition operation of the apparatus to between and ON and an OFF state. In some embodiments, a second electrical capacitance sensor that is configured to control projection of light to a half intensity and including a third capacitance sensor that is configured to control projection of light to a full intensity.

In some embodiments, the examination light apparatus includes digital logic that is configured to discriminate between background and foreground capacitance using procedures that compute at least one moving average of an amount of capacitance that is detected over time by a electrical capacitance sensor.

The invention also provides for a method of making an examination lamp apparatus that is controlled without requiring physical contact from a user, including the steps of providing a lamp head that is configured to project light, a lamp body that is configured to electrically attach to and physically support the lamp head, a lamp control component that includes an outer surface and that is configured to enable a user to control an amount of light that is projected from the lamp head without requiring physical contact between the user and the lamp control component. The control component includes at least one electrical capacitance sensor located behind the outer surface and where the control is exercised by positioning a human appendage within near proximity of the electrical capacitance sensor without the appendage making physical contact with the outer surface of the control component.

In some embodiments, the examination light apparatus includes a light emitting diode that emits light in a direction along an axis, a projector lens that is disposed along the axis and that is configured for receiving and directing the light along the axis, a molded injector lens disposed along the axis and configured for directing the light from the light emitting diode towards the projector lens along the axis, a holographic diffuser disposed along the axis and configured for directing the light towards the projector lens along the axis and a cone concentrator that is configured for receiving the light from the molded injector lens and for concentrating and directing the light towards the holographic diffuser. The invention also provides for a method for making the above described apparatus.

While the present invention has been explained with reference to the structure disclosed herein, it is not confined to the details set forth and this invention is intended to cover any modifications and changes as may come within the scope and spirit of the following claims.

What is claimed is:

1. An examination lamp apparatus that is controlled without requiring physical contact from a user, said apparatus comprising:
   a lamp head that is configured to project light;
   a lamp body that is configured to electrically attach to and physically support said lamp head;
   a base;
   a support member intermediately disposed between the base and lamp head, the lamp head being attached to one end of the support member opposite the base; and
   a lamp control component mechanically and electrically connected to the lamp head, the lamp control component including a component housing which is separately disposed from the lamp head as part of the support member and having an outer surface, the outer surface having at least one feature disposed thereon that is configured to enable a user to control an amount of light that is projected from said lamp head without requiring physical contact between said user and said lamp control component; and wherein
   said lamp control component includes at least one electrical capacitance sensor located behind said outer surface within the component housing and where said control is exercised by positioning a human appendage within near proximity of said electrical capacitance sensor without said appendage making physical contact with said outer surface of said lamp control component.

2. The examination lamp apparatus of claim 1 wherein said near proximity is a distance of 1 inch or less from said electrical capacitance sensor.

3. The examination lamp apparatus of claim 1 wherein said near proximity is a distance of 0.75 inches or less from said outer surface of said control component.

4. The examination lamp apparatus of claim 1 where said outer surface of said lamp control component includes no moving parts, excludes surface pockets and is configured to form a barrier between inner portions of said lamp control component and contamination that could be deposited upon said lamp control component via physical contact between a user and said lamp control component.

5. The examination lamp apparatus of claim 1 wherein said at least one electrical capacitance sensor is disposed inside of and proximate to a portion of said outer surface of said lamp control component, and wherein said electrical capacitance sensor is further configured to detect a capacitance of an appendage of a user being placed in physical contact with or within near proximity of, said portion of said outer surface of said lamp control component.

6. The examination lamp apparatus of claim 1 wherein said lamp head includes a variable quantity comprising one or more light emitting diodes.

7. The examination lamp apparatus of claim 6 that further comprises an LED control component that is configured to adapt to and supply an amount of electrical power, voltage and current to said variable quantity of light emitting diodes, in accordance with electrical power requirements of said variable quantity of light emitting diodes.

8. The examination lamp apparatus of claim 7 wherein said LED control component is further configured to supply an amount of electrical power, voltage and current to said variable quantity of light emitting diodes in accordance with said amount of light controlled by said user.

9. The examination lamp apparatus of claim 1 where said lamp body is configured to electrically attach to one of a plurality of lamp heads that each includes a unique arrangement and quantity of light emitting diodes, and where said LED control component is configured to adapt to and supply an amount of electrical power, voltage and current to said one of said plurality of lamp heads upon electrical attachment between said lamp body and said one of said plurality of lamp heads.

10. The examination lamp apparatus of claim 1 wherein said lamp control component is supplied from a battery.

11. The examination lamp apparatus of claim 10 where said battery is further employed as a ballast for said examination light apparatus.

12. The examination lamp apparatus of claim 11 in which said battery is configured to be attached to a universal serial bus so that status and use history of the battery is being obtained.

13. The examination lamp apparatus of claim 1 including a first electrical capacitance sensor that is configured to be toggled to transition operation of said apparatus to between and ON and an OFF state.

14. The examination lamp apparatus of claim 1 including a second electrical capacitance sensor that is configured to control projection of light to a half intensity and including a third capacitance sensor that is configured to control projection of light to a full intensity.

15. The examination lamp apparatus of claim 1, including digital logic that is configured to discriminate between background and foreground capacitance using procedures that compute at least one moving average of an amount of capacitance that is detected over time by a electrical capacitance sensor.

* * * * *